(12) United States Patent
Chen et al.

(10) Patent No.: US 6,858,619 B2
(45) Date of Patent: Feb. 22, 2005

(54) FUSED HETEROCYCLIC COMPOUNDS

(75) Inventors: Xiaoqi Chen, San Mateo, CA (US); Kang Dai, Albany, CA (US); Pingchen Fan, Fremont, CA (US); Shugui Huang, San Bruno, CA (US); Leping Li, Burlingame, CA (US); Jeffrey Thomas Mihalic, San Francisco, CA (US)

(73) Assignee: Amgen Inc., Thousand Oaks, CA (US)

( * ) Notice: Subject to any disclaimer, the term of this patent is extended or adjusted under 35 U.S.C. 154(b) by 26 days.

(21) Appl. No.: 10/138,279

(22) Filed: May 3, 2002

(65) Prior Publication Data

US 2003/0023085 A1 Jan. 30, 2003

Related U.S. Application Data

(60) Provisional application No. 60/288,665, filed on May 4, 2001.

(51) Int. Cl.$^7$ ................... C07D 471/04; A61K 31/437; A61P 3/04; A61P 25/22
(52) U.S. Cl. ........................................ 514/285; 549/70
(58) Field of Search ............................ 546/70; 514/285

(56) References Cited

FOREIGN PATENT DOCUMENTS

| JP | 2001226269 | 8/2001 |
|---|---|---|
| WO | WO 91/07966 | 6/1991 |
| WO | WO 94/07896 | 4/1994 |
| WO | WO 95/13071 | 5/1995 |
| WO | WO 96/23793 | 8/1996 |
| WO | WO 98/31684 | 7/1998 |
| WO | WO 2000/21577 | 4/2000 |
| WO | WO 2000/49046 | 8/2000 |
| WO | WO 2001/07606 | 2/2001 |
| WO | WO 2000/21169 | 3/2001 |
| WO | WO 2001/87834 | 11/2001 |
| WO | WO 2002/03070 | 1/2002 |
| WO | WO 2002/04433 | 1/2002 |
| WO | WO 2002/06245 | 1/2002 |
| WO | WO 2002/002744 | 1/2002 |
| WO | WO 2002/032897 | 4/2002 |
| WO | WO 2002/051809 | 7/2002 |
| WO | WO 2002/057233 | 7/2002 |
| WO | WO 2002/076929 | 10/2002 |
| WO | WO 2002/076947 | 10/2002 |
| WO | WO 2002/083134 | 10/2002 |
| WO | WO 2002/094799 | 11/2002 |
| WO | PCT/US02/13856 | 12/2002 |

OTHER PUBLICATIONS

Langlois et al. (Tetrahedron Letters (1975), (11), 955–8.*
Bergman et al. Acta Chemica Scandinavica, Series B; Organic Chemistry and Biochemistry (1980), B (34)10, 763–6.*
Boutin et al. (Can. J. Physiol. Pharmacol. 80: 388–395 (2002).*

Chambers et al., "Melanin–concentrating hormone is the cognate ligand for the orphan G–protein–coupled receptor SLC–1" *Nature,* (1999) 400:261–65.

Gonzales et al., "Behavioral Effects of α–MSH and MCH After Cectral Administration in the Female Rat", *Peptides,* (1996) 17:171–177.

Ishikura et al., "A Novel Entry to Pyrido [4,3–b] Carbazoles: An Efficient Synthesis of Ellipticine", Chemical Abstracts (2000) 132:Abs #237230.

Monzon et al., "Response to novelty after i.c.v. injection of melanin–concentrating hormone (MHC) in rats" *Physiol. Behav.* (1999) 67:813–817.

Aceto, MD et al., "Dependence studies of new compounds in the Rhesus monkey, rat and mouse", (1997) Department of Pharmacology and Toxicology, Medical College of Virginia Commonwealth University, pp. 363–407.

(List continued on next page.)

*Primary Examiner*—Mark L. Berch
*Assistant Examiner*—Kahsay Habte
(74) *Attorney, Agent, or Firm*—Jones Day

(57) ABSTRACT

Compounds useful in the treatment and/or prevention of a condition or disorder mediated by a G-protein coupled receptor are provided that have the formula:

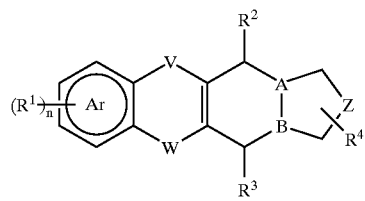

wherein

A and B are CR';

V is either a bond and W is —N(R")—, or else V is —N(R")— and W is a bond;

Z is —N(R)—CH$_2$—;

R$^1$, R$^2$, R$^3$, R$^4$, R', R", and R are as defined herein;

the subscript n is an integer from 0 to 8; and

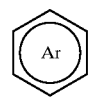

is a benzene ring.

Pharmaceutical compositions and methods of using these compounds for the treatment and/or prevention of eating disorders, obesity, anxiety disorders and mood disorders, are also provided.

47 Claims, 1 Drawing Sheet

OTHER PUBLICATIONS

Blechert, S. et al., "Domino reactions—New concepts in the synthesis of indole alkaloids and other polycyclic indole derivatives", (1995) Institut Für Organische Chemie, Sekr. C3, Technische Universität Berlin, Straβe des 17 Juni 135, D–10623 Berlin, Germany pp 592–604.

Fujii, H. et al., "A novel abnormal rearrangement in the fishcer indole synthesis", (1997) Heterocycles 45:2109–2112.

Gouyette, A. et al., "Synthesis, DNA intercalation and antitumor activity of 9–hydroxy–11–demethylellipticine and some derivatives. Comparison with the corresponding ellipticines", (1980) Eur. J. Med. Chem. 15:503–510.

Guillonneau, C. et al., "Synthesis of 9–O–substituted derivatives of 9–hydroxy–5,6–dimethyl–6H–pyrido[4,3–α] carbazole–1–carboxylic acid (2–(dimethylamino)ethyl)amide and their 10–and 11–methyl analogues with improved antitumor activity", (1990) J. Med. Chem. 42:2191–2203.

Ishikura et al., "A Novel Entry to Pyrido [4,3–b] Carbazole: An Efficient Synthesis of Ellipticine", Chemical Abstract, vol. 132, Abstract 237230, 2000.

Jones, RM et al., "6'–Guanidinonaltrindole, a highly selective and potent k–opioid receptor atagonist" (2000)Euro. J. Med. Chem. 396:49–52.

Lipkowski, AW et al., "Benzomorphan alkaloids: natural peptidomimetics of opioid pharmacophores", (1995) Letters in Peptide Science, 2:177–181.

Olmsted, SL et al., "A remarkable change of opioid receptor selectivity on the attachment of a peptidomimetic κ address element to the δ antagonist, naltrindole: 5'–[(N$^2$–alkylamidino)methyl]naltrindole derivatives as a novel class of κ opioid receptor antagonists" (1993) J. Med. Chem. 36:179–180.

Portoghese, PS et al., "Naltrindole 5'–isothiocyanate: a nonequilibrium, highly selective δ opioid receptor antagonist" (1990) J. Med. Chem. 33:1547–1548.

Portoghese, PS et al., "Design of peptidomimetic δ opioid receptor antagonists using the message–address concept" (1990) J. Med. Chem. 33:1714–1720.

Portoghese, PS et al., "Application of the message–address concept in the design of highly potent and selective non–peptide δ opioid receptor antagonists", (1988) J. Med. Chem. 31:281–282.

Portoghese, PS et al., "7'–substituted amino acid conjugates of naltrindole. Hydrophillic groups as determinants of selective antagonism of $\delta_1$ opioid receptor–mediated antinociception in mice." (1995) J. Med. Chem. 38:402–407.

Serie G Chimie Organique.—Une nouvelle synthese du systeme 6 H–pyrido–(4.3b) carbaxolique, (1972) C.R. Acad. Sc. Parism t. 274:1948–1949.

Stevens, WC et al., "Potent and selective indolomorphinan antagonists of the kappa–opioid receptor", (200) J. Med. Chem. 43:2759–2769.

Saito et al., "Molecular characterization of the melanin–concentrating–hormone receptor" Nature, (1999) 400:265–69.

Saito et al., TEM (2000) 8:299–303.

Shimada et al., "Mice lacking melanin–concentrating hormone are hypophagic and lean" Nature, (1998) 396:670–74.

* cited by examiner

FUSED HETEROCYCLIC COMPOUNDS

This application claims benefit of No. 60/288,665 filed May 4, 2001.

FIELD OF THE INVENTION

The present invention relates to compounds and compositions useful in the treatment of conditions and disorders associated with eating behavior, energy homeostasis and anxiety.

BACKGROUND OF THE INVENTION

G-protein coupled receptors play important roles in diverse signaling processes, including those involved with sensory and hormonal signal transduction. Eating disorders, which represent a major health concern throughout the world, have been linked to GPCR regulation. On the one hand, disorders such as obesity, the excess deposition of fat in the subcutaneous tissues, manifest themselves by an increase in body weight. Individuals who are obese often have, or are susceptible to, medical abnormalities including respiratory difficulties, cardiovascular disease, diabetes and hypertension. On the other hand, disorders like cachexia, the general lack of nutrition and wasting associated with chronic disease and/or emotional disturbance, are associated with a decrease in body weight.

The neuropeptide melanin-concentrating hormone (MCH), a cyclic hypothalamic peptide involved in the regulation of several functions in the brain, has previously been found to be a major regulator of eating behavior and energy homeostasis. It has previously been determined that MCH is the natural ligand for the 353-amino acid orphan G-protein-coupled-receptor (GPCR) termed SLC-1 (also known as GPR24). Subsequent to this determination, SLC-1, which is sequentially homologous to the somatostatin receptors, is frequently referred to as melanin-concentrating hormone receptor (MCH receptor, MCHR or MCHR1) (see Chambers et al., *Nature* 400:261–65 (1999); Saito et al., *Nature* 400:265–69 (1999); and Saito et al., *TEM* 11(8): 299–303 (2000)).

Compelling evidence exists that MCH is involved in regulation of eating behavior. First, intracerebral administration of MCH in rats resulted in stimulation of feeding. Next, mRNA corresponding to the MCH precursor is up-regulated in the hypothalamus of genetically obese mice and of fasted animals. Finally, mice deficient in MCH are leaner and have a decreased food intake relative to normal mice. MCH is believed to exert its activity by binding to MCHR, resulting in the mobilization of intracellular calcium and a concomitant reduction in cAMP levels (see Chambers et al., *Nature* 400:261–65 (1999); Shimada et al. *Nature* 396:670–74 (1998)). MCH also activates inwardly rectifying potassium channels, and MCHR has been found to interact with both Gαi protein and Gαq protein (Saito et al., *TEM* 11(8):299–303 (2000)). Moreover, analysis of the tissue localization of MCHR indicates that it is expressed in those regions of the brain involved in olfactory learning and reinforcement. The cumulative data suggest that modulators of MCHR should have an effect on neuronal regulation of food intake (see Saito et al., *Nature* 400:265–69 (1999)).

MCH has been shown to modulate behaviors other than feeding, such as anxiety (Gonzales et al. (1996) *Peptides* 17:171–177; Monzon et al. (1999) *Physiol. Behav.* 67:813–817).

The identification of MCHR modulators is useful for the study of physiological processes mediated by MCHR and the development of therapeutic agents for the treatment of conditions and disorders associated with weight regulation, learning, anxiety and other neuronal-related functions.

SUMMARY OF THE INVENTION

The present invention provides fused heterocyclic compounds and compositions, and methods of use thereof to treat or prevent conditions and disorders mediated by MCHR. In particular, the present invention provides compounds, compositions and methods for treating conditions and disorders associated with eating behavior, energy homeostasis and anxiety.

The compounds of the invention have the formula (I):

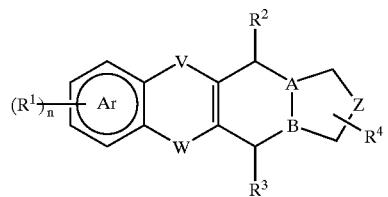

wherein

A and B are independently selected from the group consisting of CR' and N, wherein R' is selected from the group consisting of hydrogen, $(C_1–C_5)$alkyl, arylalkyl, —C(O)$R^7$, —CO$_2R^8$ and —C(O)NR$^5R^6$;

V is selected from the group consisting of a bond, —O—, —S—, —C(O)—, —N(R")— and —N═, wherein R" is hydrogen or $(C_1–C_5)$alkyl;

W is selected from the group consisting of —O—, —S—, —C(O)—, —C(S)—, —N(R")— and —N═, wherein R" is hydrogen or $(C_1–C_5)$alkyl;

Z is selected from the group consisting of —N(R)—, —N(R)—$(C_1–C_3)$alkylene- and —$(C_1–C_3)$alkylene —N(R)—$(C_1–C_3)$alkylene-, wherein R is selected from the group consisting of hydrogen, $(C_1–C_7)$alkyl, heterocycloalkyl$(C_1–C_7)$alkyl, aryl, arylalkyl, —C(O)$R^7$, —CO$_2R^8$, —C(O)NR$^5R^6$, —S(O)$_m$NR$^5R^6$ and —S(O)$_mR^7$;

each $R^1$ is independently selected from the group consisting of hydrogen, halogen, $(C_1–C_5)$alkyl, perfluoro $(C_1–C_5)$alkyl, —OR'", —SR'", aryl, arylalkyl, —NO$_2$—NR$^5R^6$, —C(O)$R^7$, —CO$_2R^8$, —C(O) NR$^5R^6$, —N(R$^5$)C(O)$R^7$, —N(R$^5$)CO$_2R^9$, —N(R$^7$)C (O)NR$^5R^6$, —S(O)$_m$NR$^5R^6$—, S(O)$_mR^7$, —CN and —N(R $^5$)S(O)$_mR^9$, wherein R'" is selected from the group consisting of hydrogen, $(C_1–C_5)$alkyl, aryl and aryl$(C_1–C_5)$alkyl;

$R^2$ and $R^3$ are independently selected from the group consisting of hydrogen, —OR'", ═O, —CN, $(C_1–C_5)$ alkyl and aryl, wherein R'" is selected from the group consisting of hydrogen, $(C_1–C_5)$alkyl, aryl and aryl $(C_1–C_5)$alkyl;

$R^4$ is selected from the group consisting of hydrogen —OR'", —C(O)$R^7$, —CO$_2R^8$, —C(O)NR$^5R^6$, —CN, $(C_1–C_5)$alkyl and aryl, wherein R'" is selected from the group consisting of hydrogen, $(C_1–C_5)$alkyl, aryl and aryl$(C_1–C_5)$alkyl;

$R^5$ and $R^6$ are independently selected from the group consisting of hydrogen, alkyl, aryl and arylalkyl or combined to form a 4-, 5-, 6-, 7- or 8-membered ring containing from one to three heteroatoms;

$R^7$ and $R^8$ are independently selected from the group consisting of hydrogen, alkyl, aryl and arylalkyl;

R⁹ is selected from the group consisting of alkyl, aryl and arylalkyl;

the subscript m is an integer from 1 to 2;

the subscript n is an integer from 0 to 8; and

represents a single or fused aryl or heteroaryl ring; with the proviso that $R_2$ is not hydrogen when

is benzene, A and B are both CH, V is a bond, W is —N(R")— and Z is —NR—CH$_2$—.

The compounds provided in the above formula are meant to include all pharmaceutically acceptable salts and prodrugs thereof.

Other objects, features and advantages of the present invention will become apparent to those skilled in the art from the following description and claims.

DETAILED DESCRIPTION OF THE INVENTION

Abbreviations and Definitions

Figure 1:
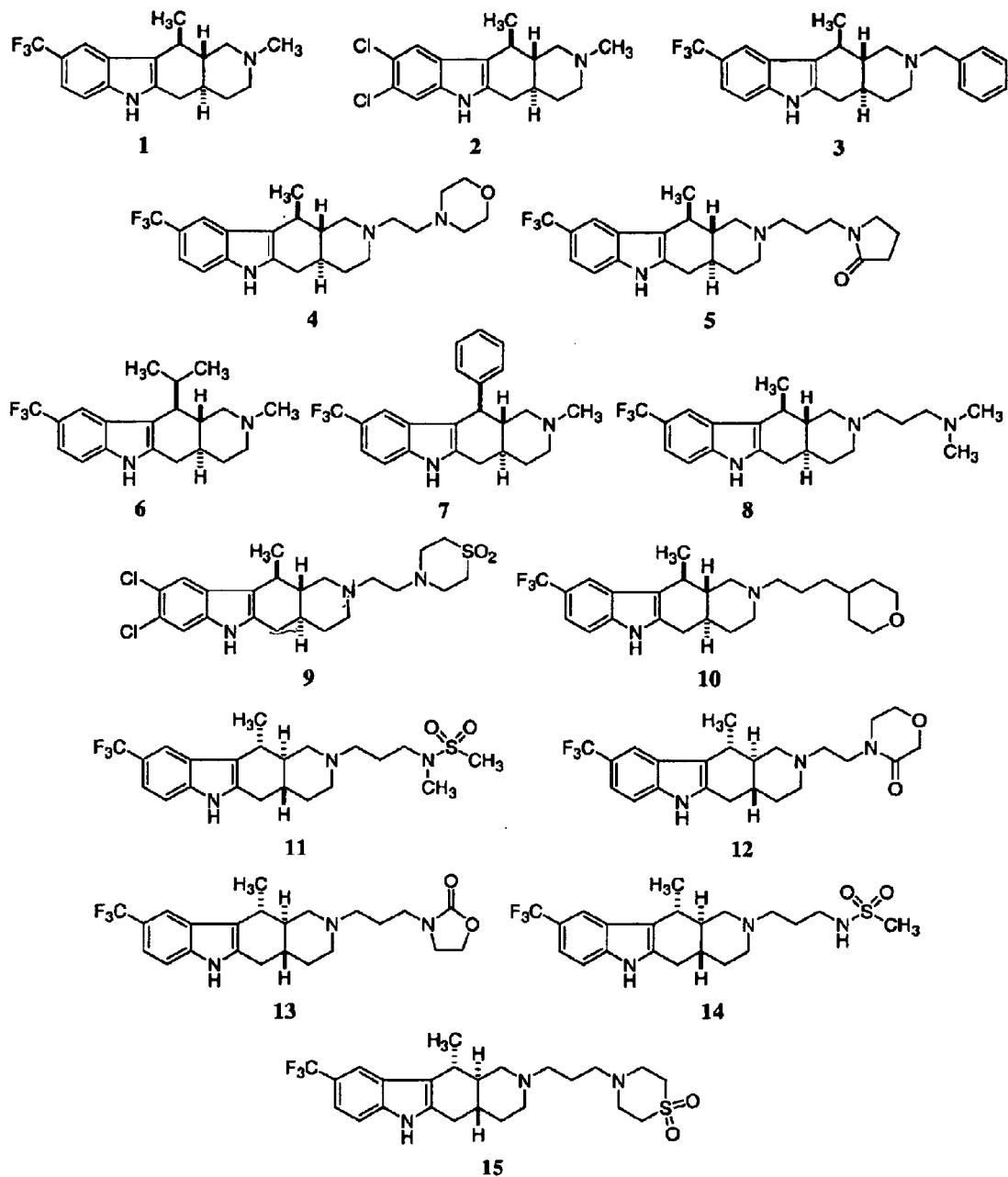
FIG. 1 provides the structures of exemplary compounds of formula I.

The abbreviations used herein are conventional, unless otherwise defined.

The term "MCHR" refers to the melanin-concentrating hormone receptor protein 1 (MCHR1), unless otherwise stated.

The terms "treat", "treating" and "treatment" refer to a method of alleviating or abrogating a disease and/or its attendant symptoms.

The terms "prevent", "preventing" and "prevention" refer to a method of decreasing the probability or eliminating the possibility that a disease will be contracted.

As used herein, the term "MCHR-mediated condition or disorder" and the like refers to a condition or disorder characterized by inappropriate, e.g., less than or greater than normal, MCHR activity. An MCHR-mediated condition or disorder may be completely or partially mediated by inappropriate MCHR activity. However, an MCHR-mediated condition or disorder is one in which modulation of MCHR results in some effect on the underlying condition or disease (e.g., an MCHR antagonist results in some improvement in patient well-being in at least some patients). Exemplary MCHR-mediated conditions and disorders include obesity, eating disorders and other behavioral disorders, such as anxiety disorders and mood disorders.

The term "therapeutically effective amount" refers to that amount of the compound being administered sufficient to prevent development of or alleviate to some extent one or more of the symptoms of the condition or disorder being treated.

As used herein, the term "obesity" refers to the excessive accumulation of body fat. Obesity may have genetic, environmental (e.g., expending less energy than is consumed) and regulatory determinants. Cardiovascular disorders, lipid disorders and metabolic disorders, such as hypertension, hyperlidemia, coronary artery disease and diabetes, are commonly associated with obesity.

As used herein, the terms "eating disorder", "feeding disorder" and the like refer to an emotional and/or behavioral disturbance associated with an excessive decrease in body weight and/or inappropriate efforts to avoid weight gain, e.g., fasting, self-induced vomiting, laxative or diuretic abuse. Depression is commonly associated with eating disorders. Exemplary eating disorders include anorexia nervosa and bulimia.

As used herein, the term "anxiety disorder" refers to an emotional and/or behavioral disturbance characterized by persistent and pervasive worry or restlessness, tension or irritability about, e.g., health, work, money or family, for no clear reason. An anxiety disorder may be accompanied by tachycardia or dyspnea. Exemplary anxiety disorders include anxiety, generalized anxiety disorder, panic attacks, panic disorder and obsessive-compulsive disorder (OCD).

As used herein, the term "mood disorder" refers to an emotional and/or behavioral disturbance characterized by persistent and pervasive bouts of euphoria and/or depression. Exemplary mood disorders include depression and bipolar disorders. Anxiety is frequently associated with mood disorders, such as depression.

The term "modulate" refers to the ability of a compound to increase or decrease the function, or activity, of MCHR. Modulation, as described herein, includes the inhibition or activation of MCHR, either directly or indirectly. Inhibitors are compounds that, e.g., bind to, partially or totally block stimulation, decrease, prevent, delay activation, inactivate, desensitize, or down-regulate signal transduction, e.g., antagonists. Activators are compounds that, e.g., bind to, stimulate, increase, open, activate, facilitate, enhance activation, sensitize or up-regulate signal transduction, e.g., agonists.

The term "alkyl", by itself or as part of another substituent, means, unless otherwise stated, a straight or branched chain, or cyclic hydrocarbon radical, or combination thereof, which may be fully saturated, mono- or poly-unsaturated and can include di- and multi-valent radicals, having the number of carbon atoms designated (i.e., $C_1$–$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail below as "heteroalkyl," "cycloalkyl" and "alkylene." The term "alkylene" by itself or as part of another substituent means a divalent radical derived from an alkane, as exemplified by —CH$_2$CH$_2$CH$_2$CH$_2$—. Typically, an alkyl group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —Si(CH3)3, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Also included in the term "heteroalkyl" are those radicals described in more detail below as "heteroalkylene" and "heterocycloalkyl." The term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini. Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 1-pyrrolidinyl, 2-pyrrolidinyl, 3-pyrrolidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "fluoroalkyl," are meant to include monofluoroalkyl and polyfluoroalkyl.

The term "aryl," employed alone or in combination with other terms (e.g., aryloxy, arylthioxy, arylalkyl) means, unless otherwise stated, an aromatic substituent which can be a single ring or multiple rings (up to three rings) which are fused together or linked covalently. The rings may each contain from zero to four heteroatoms selected from the group consisting of N, O, and S, wherein the nitrogen and sulfur atoms are optionally oxidized, and the nitrogen atom(s) are optionally quaternized. The aryl groups that contain heteroatoms may be referred to as "heteroaryl" and can be attached to the remainder of the molecule through a heteroatom Non-limiting examples of aryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl ring systems are selected from the group consisting of the group of acceptable substituents described below.

The term "arylalkyl" is meant to include those radicals in which an aryl group is attached to an alkyl group (e.g., benzyl, phenethyl, pyridylmethyl and the like) or a heteroalkyl group (e.g., phenoxymethyl, 2-pyridyloxymethyl, 3-(1-naphthyloxy)propyl, and the like).

Each of the above terms (e.g., "alkyl," "heteroalkyl" and "aryl") is meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —$CO_2$R', —CONR'R", —OC(O)NR'R", —NR"C(O)R', —NR'—C(O)NR"R'", —NR"C(O)2R', —NH—C($NH_2$)=NH, —NR'C($NH_2$)=NH, —NH—C($NH_2$)=NR', —S(O)R', —S(O)$_2$R', —S(O)$_2$NR'R", —CN and —$NO_2$ in a number ranging from zero to (2N+1), where N is the total number of carbon atoms in such radical. R', R" and R'" each independently refer to hydrogen, unsubstituted ($C_1$–$C_8$)alkyl and heteroalkyl, unsubstituted aryl, aryl substituted with 1–3 halogens, unsubstituted alkyl, alkoxy or thioalkoxy groups, or aryl-($C_1$–$C_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —$CF_3$ and —$CH_2CF_3$) and acyl (e.g., —C(O)$CH_3$, —C(O)$CF_3$, —C(O)$CH_2OCH_3$, and the like).

Similarly, substituents for the aryl groups are varied and are selected from: -halogen, —OR', —OC(O)R', —NR'R", —SR', —R', —CN, —$NO_2$, —$CO_2$R', —CONR'R", —C(O)R', —OC(O)NR'R", —NR"C(O)R', —NR"C(O)2R', —NR'—C(O)NR"R'", —NH—C($NH_2$)=NH, —NR'C($NH_2$)=NH, —NH—C($NH_2$)=NR', —S(O)R', —S(O)$_2$R', —S(O)2NR'R", —$N_3$, —CH(Ph)$_2$, perfluoro($C_1$–$C_4$)alkoxy, and perfluoro($C_1$–$C_4$)alkyl, in a number ranging from zero to the total number of open valences on the aromatic ring system; and where R', R" and R'" are independently selected from the group consisting of hydrogen, ($C_1$–$C_8$)alkyl and heteroalkyl, unsubstituted aryl, (unsubstituted aryl)—($C_1$–$C_4$)alkyl, and (unsubstituted aryl)oxy-($C_1$–$C_4$)alkyl.

Two of the substituents on adjacent atoms of the aryl ring may optionally be replaced with a substituent of the formula —T—C(O)—($CH_2$)$_q$—U—, wherein T and U are independently —NH—, —O—, —$CH_2$— or a single bond, and q is an integer of from 0 to 2. Alternatively, two of the substituents on adjacent atoms of the aryl ring may optionally be replaced with a substituent of the formula —A—($CH_2$)$_r$—B—, wherein A and B are independently —$CH_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl ring may optionally be replaced with a substituent of the formula —($CH_2$)$_s$—X—($CH_2$)$_r$, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from the group consisting of hydrogen or unsubstituted ($C_1$–$C_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al. (1977) *J. Pharm. Sci.* 66:1–19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be bioavailable by oral administration whereas the parent drug is not. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity. Additional examples include peptidyl derivatives of a compound of the invention.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, enantiomers, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

General MCHR (GenBank Accession No. U71092) is expressed in brain, at moderate levels in the eye and skeletal muscle, and in low levels in tongue and the pituitary gland. Evidence suggests that MCHR is involved in, inter alia, olfactory learning, regulation of feeding behavior and energy metabolism, regulation of the hypothalmic-pituitary-adrenocortical axis following stress, arousal and the sensation of anxiety (Saito et al., *TEM* 11(8):299–303 (2000)). The compounds of the present invention inhibit MCHR activity, and thus, are useful in, for example, the treatment or prevention of disorders associated with these processes.

EMBODIMENTS OF THE INVENTION

Compounds

In one aspect, the present invention provides compounds represented by the formula (I):

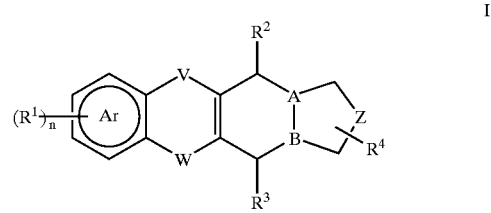

I wherein

A and B are independently selected from the group consisting of CR' and N, wherein R' is selected from the group consisting of hydrogen, ($C_1$–$C_5$)alkyl, arylalkyl, —C(O)$R^7$, —CO$_2$$R^8$ and —C(O)N$R^5$$R^6$;

V is selected from the group consisting of a bond, —O—, —S—, —C(O)—, —N(R")— and —N=, wherein R" is hydrogen or ($C_1$–$C_5$)alkyl;

W is selected from the group consisting of —O—, —S—, —C(O)—, —C(S)—, —N(R")— and —N=, wherein R" is hydrogen or ($C_1$–$C_5$)alkyl;

Z is selected from the group consisting of —N(R)—, —N(R)—($C_1$–$C_3$)alkylene- and —($C_1$–$C_3$)alkylene —N(R)—($C_1$–$C_3$)alkylene-, wherein R is selected from the group consisting of hydrogen, ($C_1$–$C_7$)alkyl, heterocycloalkyl($C_1$–$C_7$)alkyl, aryl, arylalkyl, —C(O)$R^7$, —CO$_2$$R^8$, —C(O)N$R^5$$R^6$, —S(O)$_m$N$R^5$$R^6$ and —S(O)$_m$$R^7$;

each $R^1$ is independently selected from the group consisting of hydrogen, halogen, $(C_1-C_5)$alkyl, perfluoro$(C_1-C_5)$alkyl, —OR''', —SR''', aryl, arylalkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, —S(O)$_m$R$^7$, —CN and —N(R$^5$)S(O)$_m$R$^9$, wherein R''' is selected from the group consisting of hydrogen, $(C_1-C_5)$alkyl, aryl and aryl$(C_1-C_5)$alkyl;

$R^2$ and $R^3$ are independently selected from the group consisting of hydrogen, —OR''', =O, —CN, $(C_1-C_5)$alkyl and aryl, wherein R''' is selected from the group consisting of hydrogen, $(C_1-C_5)$alkyl, aryl and aryl$(C_1-C_5)$alkyl;

$R^4$ is selected from the group consisting of hydrogen —OR''', —C(O)R$^7$, —CO$_2$R$^8$, —C(O)NR$^5$R$^6$, —CN, $(C_1-C_5)$alkyl and aryl, wherein R''' is selected from the group consisting of hydrogen, $(C_1-C_5)$alkyl, aryl and aryl$(C_1-C_5)$alkyl;

$R^5$ and $R^6$ are independently selected from the group consisting of hydrogen, alkyl, aryl and arylalkyl or combined to form a 4-, 5-, 6-, 7- or 8-membered ring containing from one to three heteroatoms;

$R^7$ and $R^8$ are independently selected from the group consisting of hydrogen, alkyl, aryl and arylalkyl;

$R^9$ is selected from the group consisting of alkyl, aryl and arylalkyl;

the subscript m is an integer from 1 to 2;

the subscript n is an integer from 0 to 8; and

represents a single or fused aryl or heteroaryl ring; with the proviso that $R_2$ is not hydrogen when

is benzene, A and B are both CH, V is a bond, W is —N(R'')— and Z is —NR—CH$_2$—.

The compounds provided in the above formula are meant to include all pharmaceutically acceptable salts and prodrugs thereof. One of skill in the art will understand that a number of structural isomers are represented by formula I. Preferred isomers are those in which

is a single aryl or heteroaryl ring and the subscript n is an integer from 0 to the maximum allowable number of substituents on ring. For example, when

is benzene, the subscript n is an integer from 0 to 4. When

is pyridine, the subscript n is an integer from 0 to 3. When

is a fused aryl or heteroaryl ring, the ring preferably contains two to three rings and the subscript n is an integer from 0 to the maximum allowable number of substituents on the ring. For example, when

is a fused aryl or heteroaryl ring containing three rings, the subscript n is an integer from 0 to 8.

In one group of preferred embodiments,

is a biaryl ring and the subscript n is an integer from 0 to 6.

In one group of preferred embodiments,

is benzene and the subscript n is an integer from 0 to 4.

In another group of preferred embodiments, A and B are both C(R').

In another group of preferred embodiments, A is C(R') and B is N.

In another group of preferred embodiments, W is N(R''). In a particularly preferred embodiment, W is NH.

In another group of preferred embodiments, V is a bond or C(O).

In another group of preferred embodiments, Z is —N(R)—CH$_2$—.

In another group of preferred embodiments, R is heterocycloalkyl$(C_1-C_7)$alkyl.

In one group of preferred embodiments, the compounds have the formula (II):

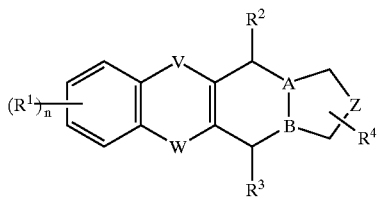

II

In another group of preferred embodiments, the compounds have the formula (III):

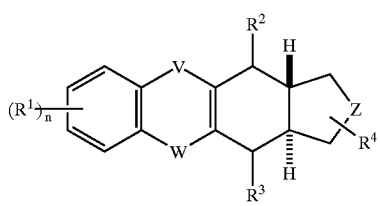

III

Still another group of preferred embodiments is represented by the formula (IV):

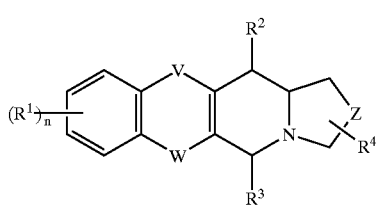

IV

In yet another group of preferred embodiments, the compounds have the formula (V):

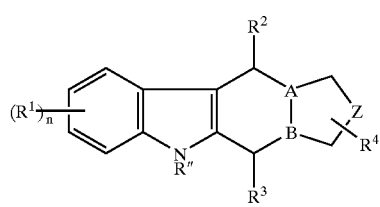

V

In yet another group of preferred embodiments, the compounds have the formula (VI):

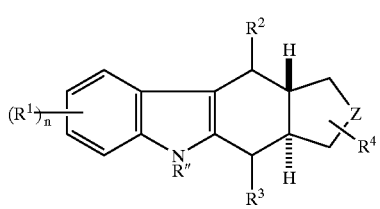

VI

In yet another group of preferred embodiments, the compounds have the formula (VII):

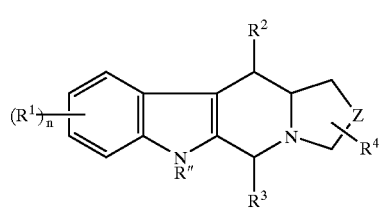

VII

In still another group of preferred embodiments, the compounds have the formula (VIII):

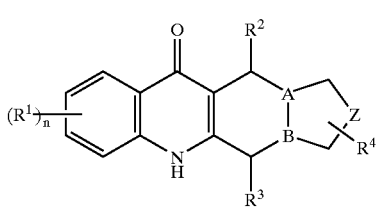

VIII

In yet another group of preferred embodiments, the compounds have the formula:

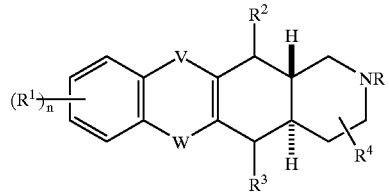

IXa or

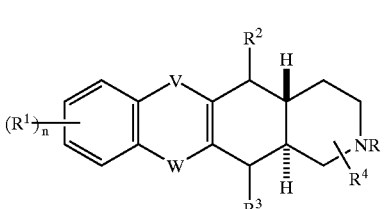

IXb

In one group of preferred embodiments, the compounds have the formula (X):

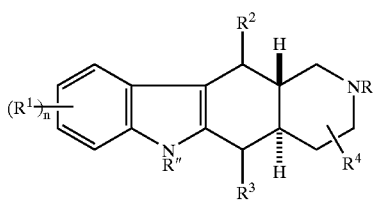

X

Exemplary structures within this preferred group of embodiments are:

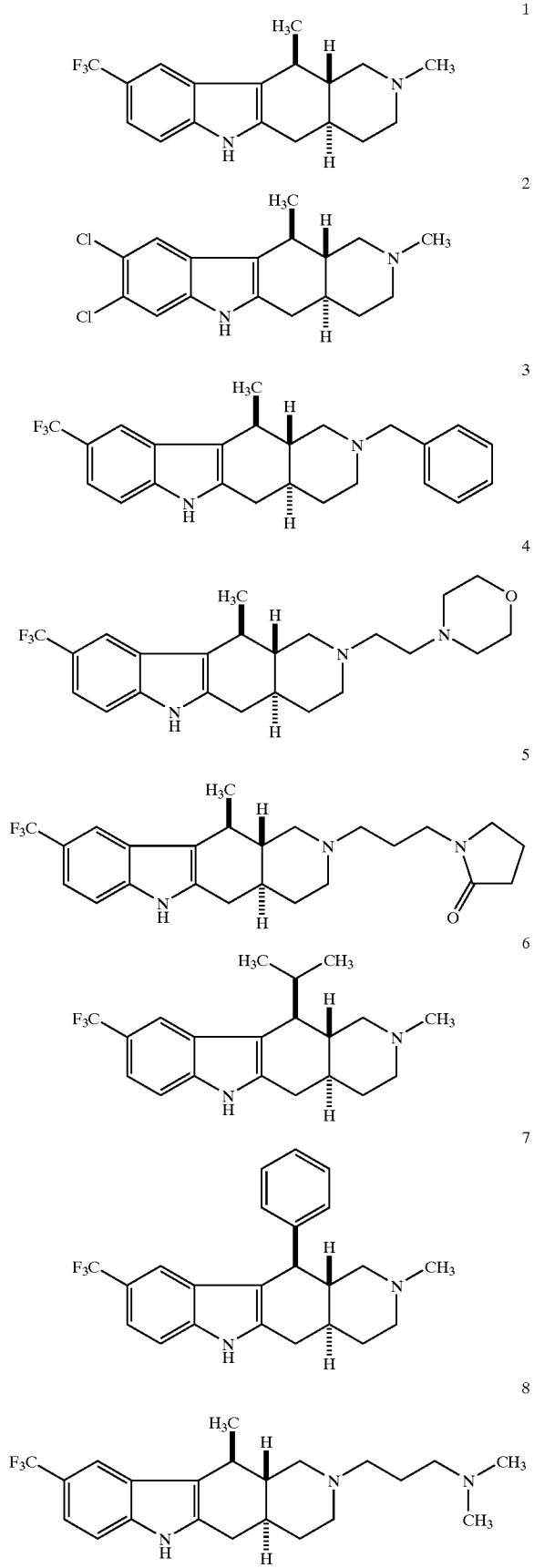
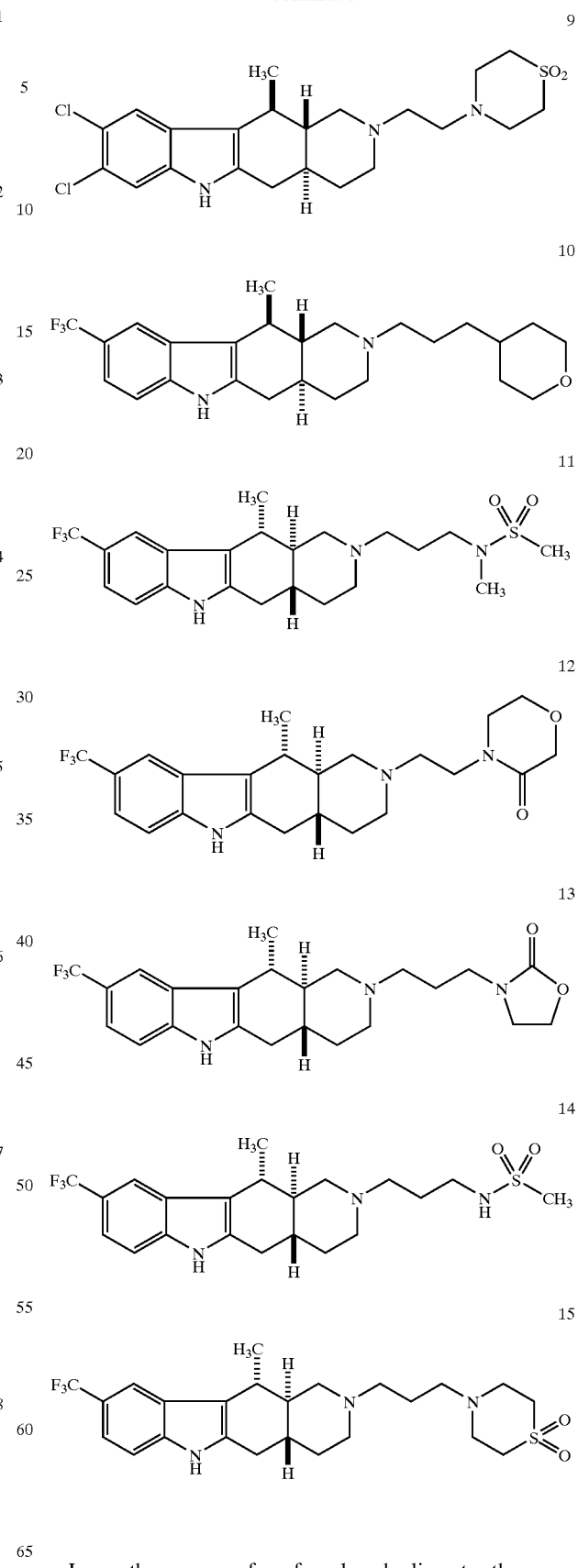
In another group of preferred embodiments, the compounds have the formula (XI):

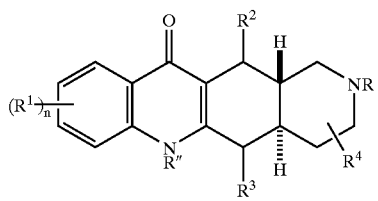

XI

Compositions

In another aspect, the present invention provides compositions comprising compounds of formula I.

The present invention provides pharmaceutical compositions which are suitable for pharmaceutical or diagnostic use. The compositions comprise compounds of formulas I–XI provided above, in combination with a diagnostically or pharmaceutically acceptable carrier or excipient. The subject compositions are useful for treating or preventing conditions and disorders mediated by MCHR, such as obesity and eating disorders, e.g., anorexia nervosa. The compounds of the present invention can be prepared and administered in a wide variety of oral and parenteral dosage forms. Thus, the compounds of the present invention can be administered by injection, for example, intravenously, intramuscularly, intracutaneously, subcutaneously, intraduodenally or intraperitoneally. Also, the compounds described herein can be administered by inhalation, for example, intranasally. Additionally, the compounds of the present invention can be administered transdermally. Other routes of administration are also contemplated for use with the compounds of the present invention, including depot administration and rectal administration.

Accordingly, the present invention also provides pharmaceutical compositions comprising a pharmaceutically acceptable carrier or excipient and either a compound of formulas I–XI or a pharmaceutically acceptable salt of a compound of formulas I–XI.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component. In tablets, the active component is mixed with the carrier having the necessary binding properties in suitable proportions and compacted in the shape and size desired.

The powders and tablets preferably contain from about 5% or 10% to 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1000 mg, preferably 1.0 mg to 100 mg according to the particular application and the potency of the active component. The composition can, if desired, also contain other compatible therapeutic agents.

In therapeutic use for the treatment of conditions and disorders mediated by MCHR, the compounds utilized in the pharmaceutical method of the invention are administered at the initial dosage of about 0.001 mg/kg to about 100 mg/kg daily. A daily dose range of about 0.1 mg/kg to about 10 mg/kg is preferred. The dosages, however, may be varied depending upon the requirements of the patient, the severity of the condition being treated, and the compound being employed. Determination of the proper dosage for a particular situation is within the skill of the practitioner. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The compositions may be advantageously combined and/or used in combination with agents useful in the treatment and/or prevention of obesity and eating disorders and pathologies associated therewith (e.g., cardiovascular disease and hypertension). In many instances, administration of the subject compounds or compositions in conjunction with these alternative agents enhances the efficacy of such agents. Accordingly, in some instances, the present compounds, when combined or administered in combination with, e.g., anti-obesity agents, can be used in dosages which are less than the expected amounts when used alone, or less than the calculated amounts for combination therapy.

Suitable agents for combination therapy include those that are currently commercially available and those that are in development or will be developed. Exemplary agents useful in the treatment of obesity include 3 adrenergic receptor agonists, leptin or derivatives thereof and neuropeptide Y antagonists. Exemplary agents useful in the treatment of anxiety and/or mood disorders include benzodiazepines, e.g., alprazolam, chlordiazepoxide, clonazepam, clorazepate, diazepam, lorazepam, oxazepam, and the like; heterocyclic antidepressants, e.g., amitriptyline, nortriptyline, imipramine, desipramine, doxepin, trimipramine, clomipramine, protryptyline, amoxapine and maprotiline; monoamine oxidase inhibitors (MAOIs), e.g., phenelzine and tranylcypromine; serotonin reuptake inhibitors (SRIs); selective serotonin reuptake inhibitors (SSRIs), e.g., fluoxetine, fluvoxamine, paroxetine and sertraline; serotonergic-noradrenergic antidepressants, e.g., venlafaxine; 5-HT2 antagonists, e.g., trazadone, nefazodone and mirtazapine; and catecholaminergic antidepressants, e.g., buproprion.

Methods of Use

In yet another aspect, the present invention provides methods of using compounds of formula I to treat or prevent a condition or disorder associated with eating behavior, energy homeostasis and anxiety. Exemplary conditions and disorders associated with eating behavior, energy homeostasis and anxiety include eating disorders, such as anorexia nervosa and bulimia, obesity, anxiety disorders, e.g., generalized anxiety disorder, panic attacks, panic disorder and obsessive-compulsive disorder (OCD), and mood disorders, e.g., depression and bipoloar disorders. Methods of using compounds of formula I to treat a condition or disorder associated with eating behavior include methods of modifying eating behavior or food intake, for example, stimulating or suppressing eating behavior or increasing or decreasing food intake. The methods comprise administering to a subject in need thereof a therapeutically effective amount of a compound of formula I.

In another aspect, the present invention provides methods of using compounds of formula I to treat or prevent a condition or disorder mediated by MCHR. The methods comprise administering to a subject in need thereof a therapeutically effective amount of a compound of formula I.

In still another aspect, the present invention provides methods of using compounds of formula I to modulate MCIR. The methods comprise contacting a cell with the compound of formula I.

The compounds of the present invention may also modulate G-protein coupled receptors related to MCHR, e.g., MCHR2 (see International Publication Nos. WO 00/49046 and WO 01/07606).

Preparation of the Compounds

The present invention provides a process for the preparation of a compound of formula I.

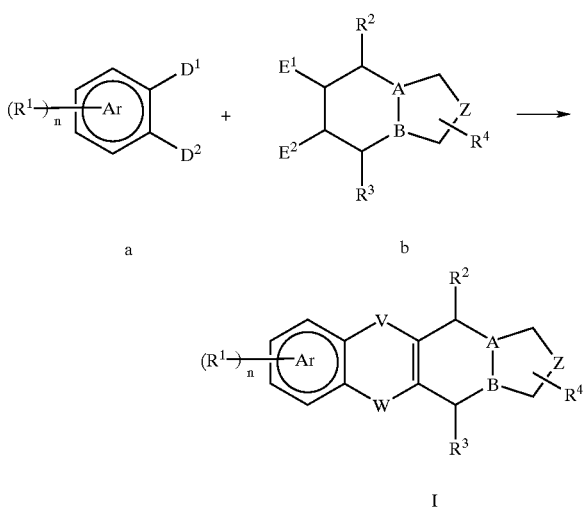

Scheme 1

A general synthetic route is depicted in Scheme 1, which comprises a condensation of substituted aryl moiety a, with a bicyclic structure b. In compound a, $D^1$ is hydrogen, halogen, —C(O)$R^7$, —CO$_2R^8$ or —C(O)N$R^5R^6$, wherein $R^5$, $R^6$, $R^7$ and $R^8$ are defined as above, and $D^2$ is a bond, —N(R")—, —N(protecting group)—, —S— or —O—, wherein R" is defined as above and protecting group is an amino protecting group. Conventional amino protecting groups consist of known groups which are used to protectively block an amino group during the synthesis procedures described herein. These conventional blocking groups are readily removable, i.e., they can be removed, if desired, by procedures which will not cause cleavage or other disruption of the remaining portions of the molecule. Suitable protecting groups for the compounds of the present invention will be recognized from the present application taking into account the level of skill in the art, and with reference to standard textbooks, such as Greene, T. W. et al. *Protective Groups in Organic Synthesis*, Wiley, New York (1991). In compound b, $E^1$ is hydrogen, —C(O)$R^7$, —CO$_2R^8$ or —C(O)N$R^5R^6$, wherein $R^5$, $R^6$, $R^7$ and $R^8$ are defined as above, and $E^2$ is =O or —N$R^5R^6$, wherein $R^5$ and $R^6$ are defined as above. When compound a, wherein $D^1$ is hydrogen and $D^2$ is —N(R")— or —N(protecting group)—, —S—, or —O— reacts with compound b, wherein $E^1$ is hydrogen and $E^2$ is =O, under the typical Fisher indolization conditions a compound of formula I is produced, wherein V is a bond and W is a bond, —N(R")—, —N(protecting group)—, —S—, or —O—. Alternatively, a similar transformation is achieved under milder conditions prior to the condensation to compound a. A preferred method is to use a precursory group in the place of Z and transform such a group into the desired Z later in the synthesis.

One of skill in the art will understand that the synthesis provided above can be modified to use different starting materials and alternate reagents to accomplish the desired transformations. Accordingly, the synthesis and reagents described herein are all expressed as non-limiting embodiments.

Materials represented by compound a are available commercially (Aldrich Chemical), or can be obtained synthetically following literature procedures.

One way to prepare compounds represented by compound b is by the Robinson annulation process between a cyclic ketone and a substituted enone followed by saturation of the double bond. One of the skill in the art will readily appreciate that other methods are available. The relative stereochemistry and absolute stereochemistry can be controlled in the process. The individual forms of the compound b, e.g., diastereomers and enantiomers, can be formed by stereo-controlled reactions, or may be separated, e.g., by chromatographic techniques (diastereomers) and by resolution (enantiomers).

Analysis of the Compounds

The activity of MCHR polypeptides can be assessed using a variety of in vitro and in vivo assays to determine functional, chemical, and physical effects, e.g., measuring ligand binding (e.g., radioactive ligand binding), second messenger (e.g., cAMP, cGMP, $IP_3$, DAG, or $Ca^{2+}$) levels, ion flux, phosphorylation levels, transcription levels, neurotransmitter levels, and the like. Furthermore, such assays can be used to test for inhibitors and activators of MCHR. Screening assays may be used to identify modulators that can be used as therapeutic agents, e.g., antagonists of MCHR activity.

Modulators of MCHR activity can be tested using MCHR polypeptides as described above, either recombinant or naturally occurring. The protein can be isolated, expressed in a cell, expressed in a membrane derived from a cell, expressed in tissue or in an animal, either recombinant or naturally occurring. For example, kidney cells, liver cells, colon cells, transformed cells, or membranes can be used. Modulation is tested using one of the in vitro or in vivo assays described herein. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Gene amplification can also be examined. Furthermore, ligand-binding domains of the protein of interest can be used in vitro in soluble or solid state reactions to assay for ligand binding.

Ligand binding to MCHR, a domain, or chimeric protein can be tested in solution, in a bilayer membrane, attached to a solid phase, in a lipid monolayer, or in vesicles. Binding of a modulator can be tested using, e.g., changes in spectroscopic characteristics (e.g., fluorescence, absorbance, refractive index) hydrodynamic (e.g., shape), chromatographic, or solubility properties.

MCHR-G-protein interactions can also be examined, by, for example, analysis of binding of the G-protein to MCHR or its release from MCHR can be examined. For example, in the absence of GTP, an activator will lead to the formation of a tight complex of a G protein (all three subunits) with MCHR. This complex can be detected in a variety of ways, as noted above. Such an assay can be modified to search for inhibitors. In one embodiment, an activator is added to MCHR and G protein in the absence of GTP, allowed to form a tight complex, and then screened for inhibitors by looking at dissociation of the MCHR-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by Gq and other cognate G proteins, and modulation of diverse channels by Gi and other G proteins. Downstream consequences can also be examined such as generation of diacyl glycerol and IP3 by phospholipase C, and in turn, for calcium mobilization by IP3.

Activated MCHR becomes a substrate for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. For a general review of GPCR signal transduction and methods of assaying signal transduction, see, e.g., *Methods in Enzymology*, vols. 237 and 238 (1994) and volume 96 (1983); Bourne et al., *Nature* 10:349:117–27 (1991); Bourne et al., *Nature* 348:125–32 (1990); Pitcher et al., *Annu. Rev. Biochem.* 67:653–92 (1998).

Samples or assays that are treated with a potential MCHR inhibitor or activator are compared to control samples without the test compound, to examine the extent of modulation. Control samples (untreated with activators or inhibitors) are assigned a relative MCHR activity value of 100. Inhibition of MCHR is achieved when the MCHR activity value relative to the control is about 90%, optionally 50%, optionally 25–0%. Activation of MCHR is achieved when the MCHR activity value relative to the control is 110%, optionally 150%, 200–500%, or 1000–2000%.

Changes in ion flux may be assessed by determining changes in polarization (i.e., electrical potential) of the cell or membrane expressing MCHR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575–1595 (1997)). Whole cell currents are conveniently determined using the standard methodology (see, e.g., Hamil et al., *PFlugers. Archiv.* 391:85 (1981). Other known assays include radiolabeled ion flux assays and fluorescence assays using voltage-sensitive dyes (see, e.g., Vestergarrd-Bogind et al., *J. Membrane Biol.* 88:67–75 (1988); Gonzales & Tsien, *Chem. Biol.* 4:269–277 (1997); Daniel et al., *J. Pharmacol. Meth.* 25:185–193 (1991); Holevinsky et al., *J. Membrane Biology* 137:59–70 (1994)). Generally, the compounds to be tested are present in the range from 1 pM to 100 mM.

The effects of the test compounds upon the function of the polypeptides can be measured by examining any of the parameters described above. Any suitable physiological change that affects MCHR activity can be used to assess the influence of a test compound on the polypeptides of this invention. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, IP3 or cAMP.

Preferred assays for MCHR include cells that are loaded with ion- or voltage-sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion-sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as Gα15 and Gα16 can be used in the assay of choice (Wilkie et al., *Proc. Natl Acad. Sci. USA* 88:10049–10053 (1991)). Such promiscuous G-proteins allow coupling of a wide range of receptors to signal transduction pathways in heterologous cells.

Receptor activation typically initiates subsequent intracellular events, e.g., increases in second messengers such as IP3, which releases intracellular stores of calcium ions. Activation of some G-protein coupled receptors stimulates the formation of inositol triphosphate (IP3) through phospholipase C-mediated hydrolysis of phosphatidylinositol (Berridge & Irvine, *Nature* 312:315–21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868–9872 (1991) and Dhallan et al., *Nature* 347:184–187 (1990)). In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.* 270:15175–15180 (1995) may be used to determine the level of cAMP. Also, the method described in Felley-Bosco et al., *Am. J. Resp. Cell and Mol. Biol.* 11:159–164 (1994) may be used to determine the level of cGMP. Further, an assay kit for measuring cAMP and/or cGMP is described in U.S. Pat. No. 4,115,538, herein incorporated by reference. In another embodiment, phosphatidyl inositol (PI) hydrolysis can be analyzed according to U.S. Pat. No. 5,436,128, herein incorporated by reference.

In another embodiment, transcription levels can be measured to assess the effects of a test compound on signal transduction. A host cell containing the protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured by using any method known to those of skill in the art to be suitable. For example, mRNA expression of the protein of interest may be detected using northern blots or their polypeptide products may be identified using immunoassays. Alternatively, transcription based assays using a reporter gene may be used as described in U.S. Pat. No. 5,436,128, herein incorporated by reference. The reporter genes can be, e.g., chloramphenicol acetyltransferase, firefly luciferase, bacterial luciferase, β-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961–964 (1997)).

The amount of transcription is then compared to the amount of transcription in either the same cell in the absence of the test compound, or it may be compared with the amount of transcription in a substantially identical cell that lacks the protein of interest. A substantially identical cell may be derived from the same cells from which the recombinant cell was prepared but which had not been modified by introduction of heterologous DNA. Any difference in the amount of transcription indicates that the test compound has in some manner altered the activity of the protein of interest.

Combinatorial Libraries

In one preferred embodiment, high throughput screening methods involve providing a combinatorial chemical or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487–493 (1991) and Houghton et al., *Nature* 354:84–88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909–6913 (1993)), vinylogous polypeptides (Hagihara et al., *J. Amer.*

Chem. Soc. 114:6568 (1992)), nonpeptidyl peptidomimetics with glucose scaffolding (Hirschmann et al., *J. Amer. Chem. Soc.* 114:9217–9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309–314 (1996) and PCT/US96/10287), carbohydrate libraries (see, e.g., Liang et al., *Science*, 274:1520–1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. Nos. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass. 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.)

High Throughput Screening

High throughput assays for the presence, absence, quantification, or other properties of particular compounds may be used to test a combinatorial library that contains a large number of potential therapeutic compounds (potential modulator compounds). The assays are typically designed to screen large chemical libraries by automating the assay steps and providing compounds from any convenient source to assays, which are typically run in parallel (e.g., in microtiter formats on microtiter plates in robotic assays). Preferred assays detect activation or inhibition of MCHR activity.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5–10 wells can test a single modulator. Thus, a single standard microtiter plate can assay about 100 (e.g., 96) modulators. If 1536 well plates are used, then a single plate can easily assay from about 100—about 1500 different compounds. It is possible to assay several different plates per day; assay screens for up to about 6,000–20,000 different compounds is possible using the integrated systems of the invention.

The molecule of interest can be bound to the solid state component, directly or indirectly, via covalent or noncovalent linkage e.g., via a tag. The tag can be any of a variety of components. In general, a molecule which binds the tag (a tag binder) is fixed to a solid support, and the tagged molecule of interest (e.g., the signal transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue (SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors can be used in forming immobilizable tag and capture moiety pairs. For instance, cell receptor-ligand interactions, such as transferrin, c-kit, viral receptor ligands, cytokine receptors, chemokine receptors, interleukin receptors, immunoglobulin receptors and antibodies, the cadherin family, the integrin family and the selectin family, can all be employed in the methods of the present invention (see, e.g., Pigott & Power, *The Adhesion Molecule Facts Book* 1 (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethelyne glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149–2154 (1963) (describing solid phase synthesis of, e.g., peptides); Geysen et al., *J. Immun. Meth.* 102:259–274 (1987) (describing synthesis of solid phase components on pins); Frank & Doring, *Tetrahedron* 44:60316040 (1988) (describing synthesis of various peptide sequences on cellulose disks); Fodor et al., *Science*, 251:767–777 (1991); Sheldon et al., *Clinical Chemistry* 39(4):718–719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Yet another assay for compounds that modulate MCHR activity involves computer assisted drug design, in which a computer system is used to generate a three-dimensional structure of MCHR based on the structural information encoded by the amino acid sequence. The input amino acid sequence interacts directly and actively with a preestablished algorithm in a computer program to yield secondary, tertiary, and quaternary structural models of the protein. The models of the protein structure are then examined to identify regions of the structure that have the ability to bind, e.g., modulators. These regions are then used to identify modulators that bind to the protein.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential ligand binding regions are identified by the computer system. Three-dimensional structures for potential ligands are generated by entering amino acid or nucleotide sequences or chemical formulas of compounds, as described above. The three-dimensional structure of the potential ligand is then compared to that of the GPCR protein to identify ligands that bind to GPCR. Binding affinity between the protein and ligands is determined using energy terms to determine which ligands have an enhanced probability of binding to the protein.

The following examples are provided by way of illustration only and not by way of limitation. Those of skill in the art will readily recognize a variety of noncritical parameters that could be changed or modified to yield essentially similar results.

EXAMPLES

Reagents and solvents used below can be obtained from commercial sources such as Aldrich Chemical Co. (Milwaukee, Wis., U.S.A.). $^1$H-NMR spectra were recorded on a Varian Gemini 400 MHz NMR spectrometer. Significant peaks are tabulated in the order: multiplicity (s, singlet; d, doublet; t, triplet; q, quartet; m, multiplet; br s, broad singlet), coupling constant(s) in Hertz (Hz) and number of protons. Electron Ionization (EI) mass spectra were recorded on a Hewlett Packard 5989A mass spectrometer. Mass spectrometry results are reported as the ratio of mass over charge, followed by the relative abundance of each ion (in parentheses). A single m/e value is reported for the M+H (or, as noted, M−H) ion containing the most common atomic isotopes. Isotope patterns correspond to the expected formula in all cases. Electrospray ionization (ESI) mass spectrometry analysis was conducted on a Hewlett-Packard 1100 MSD electrospray mass spectrometer using the HP1 100 HPLC for sample delivery. Normally the analyte was dissolved in methanol at 0.1 mg/mL and 1 microliter was infused with the delivery solvent into the mass spectrometer, which scanned from 100 to 1500 daltons. All compounds could be analyzed in the positive ESI mode, using 1:1 acetonitrile/water with 1% acetic acid as the delivery solvent. The compounds provided below could also be analyzed in the negative ESI mode, using 2 mM $NI_4OAc$ in acetonitrile/water as delivery solvent. Analytical HPLC analysis was conducted on a Hewlett-Packard Series 1050 system equipped with a C18 reverse phase column (4.6 mm×150 mm) manufactured by Shiseido Co., Japan. Gradient elution was performed using variable percentage of acetonitrile and water (each with 0.1% trifluoroacetic acid added) as a mobile phase. Optical purity analysis was also conducted on a Hewlett-Packard Series 1050 system equipped with a chiral HLPC column (ChiralPak AD, 4.6 mm×150 mm) purchased from Chiral Technology. Isopropanol (3%) and hexane (97%) containing 0.1% diethylamine was used as a mobile phase.

Example 1

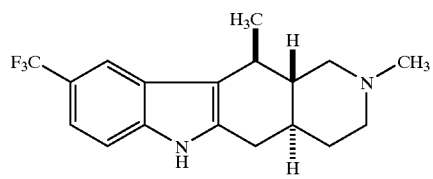

1

Compound 1 was synthesized in three steps according to Scheme 2 (*Acta. Chem. Scand. B*, 34, 1980, 136). To a mixture of NaH (2.44 g, 61 mmol, in 60% mineral oil) in ether (200 mL) at room temperature was added 1-methyl-4-piperidone (7.38 ml, 60 mmol) via syringe. After stirring for 1 h at room temperature, the reaction mixture was cooled to 0° C. 3-Penten-2-one (5.00 g, 60 mmol, contains 30% mesityl oxide) was added to the reaction mixture via syringe. The mixture was kept at 0° C. overnight. The reaction mixture was poured into aqueous $NaHCO_3$ and extracted with EtOAc. The organic layer was separated, washed with brine, dried with anhydrous $Na_2SO_4$, concentrated by rotary evaporation and purified by flash chromatography on silica gel with a gradient elution of 10–50% MeOH/EtOAc mixed with 0–20% conc. ammonia to yield enone i, wherein R is a methyl group, as a yellowish oil (2.66 g).

Scheme 2

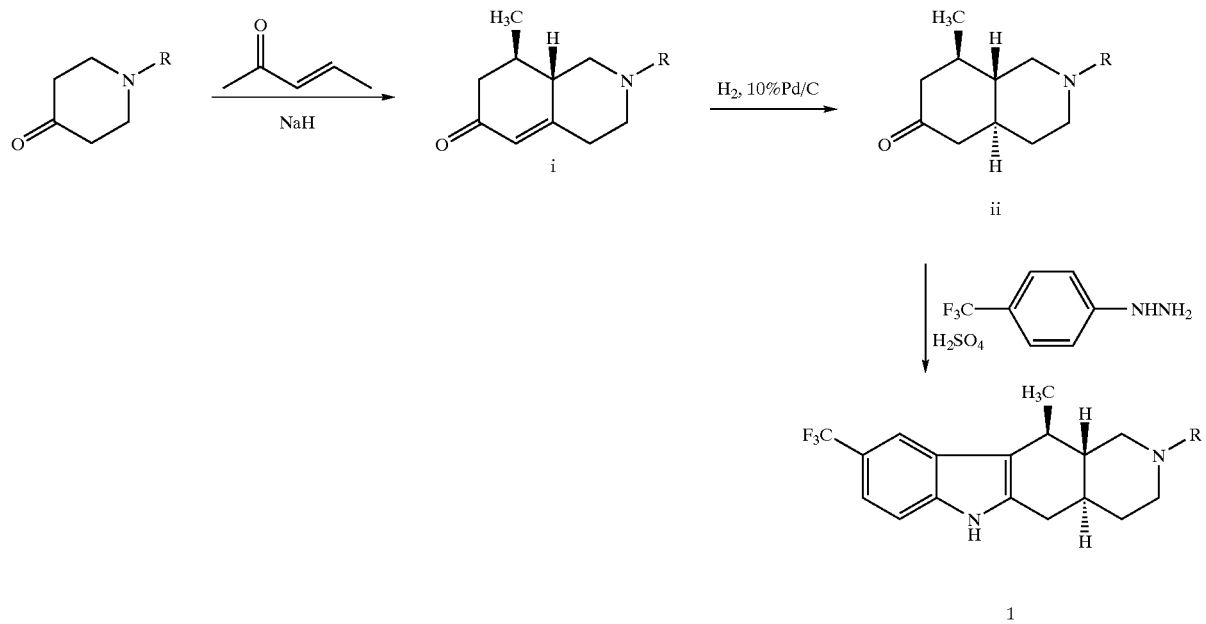

Enone i (2.60 g, 14.52 mmol) was stirred with 10% Pd/C (0.300 g) in EtOH (100 mL under balloon $H_2$ for 2.5 days. The reaction mixture was filtered. The filtrate was collected, concentrated by rotary evaporation and purified by flash chromatography on silica gel with a gradient elution of 20–40% $MeOH/CH_2Cl_2$ mixed with 0–20% conc. ammonia to yield the corresponding ketone ii as a yellowish solid (1.955 g).

A mixture of ketone ii (0.073 g, 0.4 mmol), 4-(trifluoromethyl)phenylhydrazine (0.070 g, 0.4 mmol), conc. $H_2SO_4$ (2 drops) and MeOH (2 mL) was stirred at room temperature overnight. Two more drops of $H_2SO_4$ were added and the mixture was heated to 80° C. in a sealed vial for 2 h. The mixture was cooled to room temperature, basified with aqueous $NaHCO_3$ and extracted with EtOAc. The organic layer was separated, washed with brine, dried with anhydrous $Na_2SO_4$, concentrated by rotary evaporation and purified by flash chromatography on silica gel with a gradient elution of 20–50% $MeOH/CH_2Cl_2$ mixed with 0–15% conc. ammonia to yield compound 1 as a pink solid (0.095 g). $^1H$ NMR (DMSO-$d_6$): δ 11.20 (s, 1H), 7.78 (s, 1H), 7.43 (d, J=8.4 Hz, 1H), 7.28 (d, J=8.4 Hz, 1H), 3.20 (m, 1H), 2.83 (m, 1H), 2.74 (m, 1H), 2.60 (m, 1H), 2.19 (m, 1H), 2.26 (s, 3H), 1.92 (m, 1H), 1.81 (m, 1H), 1.70 (m, 1H), 1.38 (m, 3H), 1.36 (d, J=6.7 Hz, 1H). MS (ES): 323 [M+H]$^+$.

Alternatively, compound 1 can be prepared enantioselectively by performing a resolution of enone i. A general procedure for resolving enone i, wherein R is hydrogen, is described below.

To a stirred hot solution of the racemic isoquinolinone free base i (60.8 g, 0.239 mol) in 95% ethanol (150 mL) was added solution of di-O-p-toluoyl-L-tartaric acid (92.1 g, 0.124 mol) in hot ethanol (100 mL). Precipitation of the less soluble diasteromeric salt occurred soon after. The mixture was heated in a hot (80° C.) water bath with gentle stirring for 1 h, allowing some solvent to escape. The mixture was allowed to cool to room temperature slowly over several hours. The precipitate (52.9 g) was collected by filtration, triturated with hot 95% ethanol (150 mL) and collected by filtration after cooling. The solid salt collected was triturated with 100 mL 95% ethanol (hot), after cooling the solid was collected again by filtration. The free base (22.3 g, 0.087 mol) was obtained after neutralization with aqueous $NaHCO_3$ and extraction with AcOEt. The optical purity of the resolved product was determined to 96% ee by chiral HPLC analysis.

Example 2

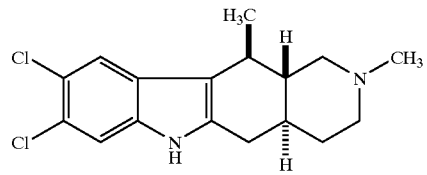

The title compound was synthesized according to Example 1, starting from ketone ii (Scheme 2), wherein R is a methyl group (0.063 g, 0.35 mmol), and 3,4-dichlorophenylhydrazine (0.960 g, 0.45 mmol). Cyclization was completed in 5 h at 80° C. Purification was performed by flash chromatography with a gradient elution of 20–50% $MeOH/CH_2Cl_2$ mixed with 0–15% conc. ammonia followed by reverse-phased HPLC to yield compound 2 as a yellowish solid (0.007 g). $^1H$ NMR (DMSO-$d_6$): δ 11.07 (s, 1H), 7.68 (s, 1H), 7.48 (s, 1H), 3.18 (m, 1H), 2.80 (m, 1H), 2.75 (m, 1H), 2.35 (m, 1H), 2.23 (s, 3H), 1.70 (m, 2H), 1.60 (m, 1H), 1.40 (m, 2 H), 1.33 (d, J=6.6 Hz, 1H), 1.11 (m, 1H), 0.80 (m, 1H). MS (ES): 323 [M+H]$^+$.

Example 3

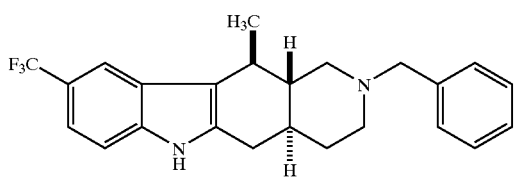

Compound 3 was synthesized according to Example 1, using 1-benzylpiperidin-4-one as the starting material. $^1$H NMR (DMSO-d$_6$): δ 11.2 (s, 1H), 7.76 (s, 1H), 7.43 (s, 1H), 7.35 (bs, 5H), 3.59 (d, J=12 Hz, 1H), 3.46 (d, J=12 Hz, 1H), 3.26 (m, 2H), 2.83 (d, J=5.0 Hz, 1H), 2.75 (dd, J=15, 2 Hz, 1H), 2.60 (t, J=3 Hz, 1H), 2.42 (dd, J=15, 8 Hz, 1H), 1.95 (t, J=5 HZ, 1H), 1.80 (m, 2H), 1.46 (m, 2H), 1.46 (bs, 2H), 1.29 (d, J=6.6 Hz, 3H). MS (ES): 399 [M+H]$^+$.

Example 4

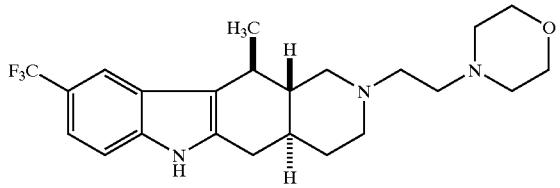

Compound 4 was prepared in two steps from compound 3, as follows.

Scheme 3

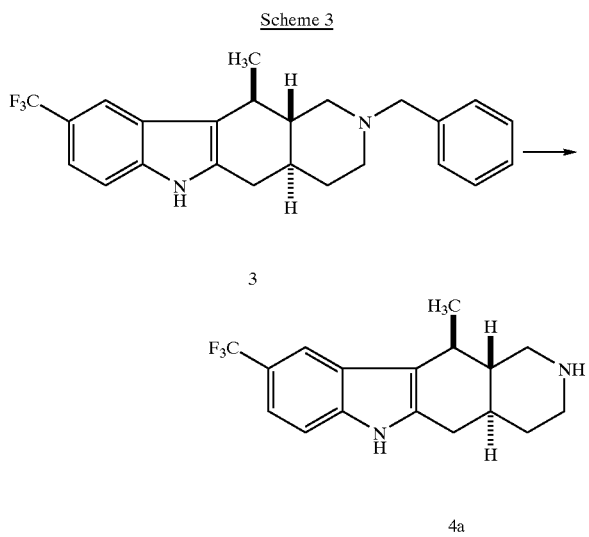

Step A

A mixture of compound 3 (3.80 g, 9.55 mmol), HCO$_2$NH$_4$ (3.03 g, 48 mmol), 10% Pd/C (0.380 g) and MeOH (150 mL) was refluxed for 7 h. The reaction mixture was cooled to room temperature, basified with saturated aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20–50% MeOH—CH$_2$Cl$_2$ mixed with 0–15% conc. ammonia to yield the corresponding free amine (4a) as a yellowish solid (2.50 g). $^1$H NMR (DMSO-d$_6$)δ 11.2 (s, 1H), 7.80 (s, 1H), 7.43 (d, J=5.4 Hz, 1H), 7.28 (d, J=5.4 Hz, 1H), 3.40 (d, J=6.0 Hz, 1H), 3.01 (d, J=8.0 Hz, 1H), 2.75 (d, J=10 Hz, 1H), 2.60 (m, 2H), 2.40 (m, 2H), 1.82 (d, J=8 Hz, 1H), 1.56 (m, 1H), 1.38 (d, J=5.4 Hz, 3H), 1.25 (m, 2H). MS (ES): 309 [M+H]$^+$.

Scheme 4

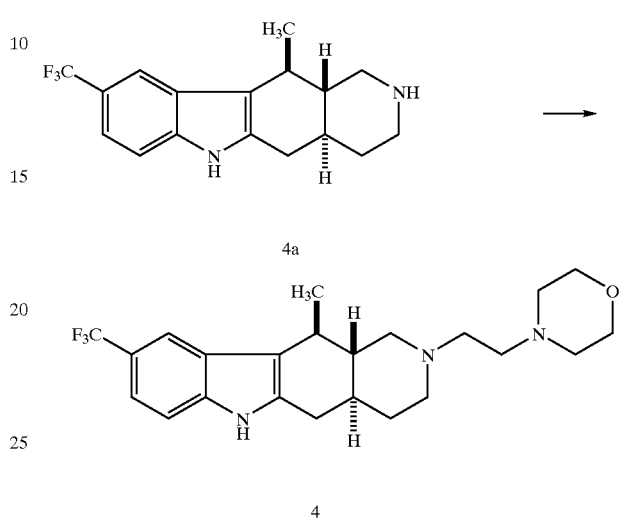

Step B

The product of step A (4a) (1.52 g, 4.94 mmol) was treated with N-2-chloroethylmorpholine hydrochloride (0.964 g, 5.19 mmol), NaI (0.22 g, 1.48 mmol), NaHCO$_3$ (1.03 g, 12.5 mmol), in acetone (50 mL) for 15 h at refluxing temperature. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20–50% MeOH/EtOAc mixed with 0–15% conc. ammonia to yield compound 4 as a yellowish solid (0.68 g). $^1$H NMR (DMSO-d$_6$): δ 11.2 (s, 1H), 7.77 (s, 1H), 7.43 (d, J=6.4 Hz, 1H), 7.24 (d, J=6.4 Hz, 1H), 3.79 (bs, 4H), 2.90 (bs, 1H), 2.75 (d, J=5 Hz, 1H), 2.60 (d, J=2 Hz, 1H), 2.45 (m, 8H), 2.38 (bs, 4H0, 1.92 (m, 1H), 1.80 (m, 1H), 1.75 (m, 1H), 1.40 (m, 1H), 1.38 (d, J=5.0 Hz, 3H), 1.25 (m, 2H). MS (ES): 422 [M+H]$^+$.

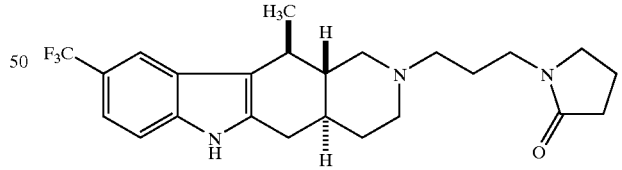

Example 5

The secondary amine (4a) from step A of Example 4 (0.040 g, 0.13 mmol) was treated with 2-(3-chloropropyl) pyrrolidinone (0.100 g, 0.62 mmol), NaI (0.010 g, 0.07 mmol), NaHCO$_3$ (0.080 g, 0.095 mmol), DMF (1 mL) and MeOH (1 mL) in a sealed vial for 5 h at 90° C. The reaction mixture was poured into aqueous NaHCO$_3$ and extracted with EtOAc. The organic layer was separated, washed with brine, dried with anhydrous Na$_2$SO$_4$, concentrated by rotary evaporation and purified by flash chromatography on silica gel with a gradient elution of 20–50% MeOH/EtOAc mixed with 0–15% conc. ammonia to yield the target compound as a yellowish solid (0.017 g). $^1$H NMR (DMSO-d$_6$):δ 11.19 (s, 1H), 7.77 (s, 1H), 7.43 (d, J=8.4 Hz, 1H), 7.26 (d, J=8.4 Hz, 1H), 3.18–3.40 (m, 8H), 2.91 (m, 1H), 2.72 (m, 1H), 2.60 (m, 1H), 2.39 (m, 1H), 2.30 (m, 1H), 2.21 (m, 2H), 1.92 (m, 2H), 1.81 (m, 1H), 1.66 (m, 2H), 1.41 (m, 2H),1.36 (d, J=6.7 Hz, 3H), 1.29 (m, 1H). MS (ES): 434 [M+H]$^+$.

Example 6

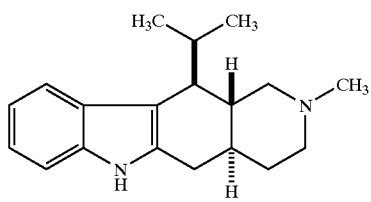

6

Compound 6 was synthesized according to Example 1, substituting 5-methyl-3-hexen-2-one for 3-penten-2-one. $^1$H NMR (DMSO-d$_6$):δ 10.68 (s, 1H), 7.36 (d, J=8.9 Hz, 1H), 7.23 (d, J=7.7 Hz, 1H), 6.95 (m, 1H), 6.88 (m, 1H), 3.15 (m, 1H), 2.87 (m, 1H), 2.61 (m, 2H), 2.27 (m, 5H), 1.97 (m, 1H), 1.79 (m, 2H), 1.52 (m, 2 H), 1.20 (m, 1H), 0.91 (d, J=7.0 Hz, 3H), 0.76 (d, J=6.9 Hz, 3H). MS (ES): 283 [M+H]$^+$.

Example 10

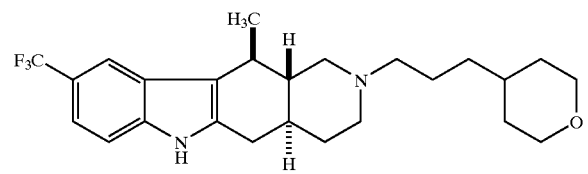

10

Compound 10 was synthesized following the procedure described in Example 5, substituting 3-(tetrahydropyran-4-yl)propyl tosylate for 1-(3-chloropropyl)pyrrolidin-2-one. $^1$H NMR of 10.HCl: (CD$_3$OD)δ 7.79 (s), 7.39 (d, J=8.6 Hz, 1H), 7.30 (d, J=8.6 Hz, 1H), 3.95 (dd, J=11, 3.7 Hz, 2H), 3.88 (d, J=11.2 Hz, 1H), 3.66 (d, J=10.3 Hz, 1H), 3.42 (td, J=12.0, 1.7 Hz, 2H), 3.20 (m, 2H), 3.03 (m, 1H), 2.89 (dd, J=16.0, 4.5 Hz, 2H), 2.82 (t, J=6.8 Hz, 1H), 2.53 (dd, J=16.2, 11.4 Hz, 1H), 2.20 (d, J=13.4 Hz, 1H), 1.86 (m, 3H), 1.74 (q, J=12.0 Hz, 1H), 1.70 (m, 3H), 1.61 (m, 1H), 1.50 (d, J=6.7 Hz, 3H), 1.37 (q, J=7.8 Hz, 2H), 1.30 (qd, J=12.1, 4.3 Hz, 2H). MS (ES) 435 [M+H]$^+$.

3-(Tetrahydropyan-4-yl)propyl tosylate can be coveniently propared using the following procedure or a variation thereof.

Tetrahydropyan-4-ylmethanol was obtained from the reduction of tetrahydropyan-4-carboxylic acid with borane or from the reduction of methyl tetrahydropyran-4-ylcarboxylate with LiAlH4.

To a solution of tetrahydropyan-4-ylmethanol (10 g, 86.2 mmol) in CH$_2$Cl$_2$ (170 mL) was added p-toluenesulfonyl chloride (17.26 g, 90.5 mmol), triethylamine (9.58 g, 94.8 mmol) and DMAP (0.527 g, 4.31 mmol). The mixture was stirred at room temperature for 16 h. Dilute aqueous NaHCO$_3$ was added and layers were separated. The organic layer was washed with brine, dried over MgSO$_4$ and concentrated to give the tetrahydropyan-4-ylmethyl tosylate as a solid.

To a suspension of CuBr (22.8 g, 158.9 mmol) in anhydrous ether cooled in an ice-water bath was added a solution of allylmagnesium bromide (1M in ether, 328 mL, 318 mmol), followed by a solution of tetrahydropyan-4-ylmethyl tosylate in ether (200 mL) and THF (100 mL). The mixture was stirred vigorously at 0° C. for 4 h (additional Grignard reagent can be added to drive the reaction to completion). The reaction was quenched by slow addition of saturated aqueous NH$_4$Cl. The mixture was filtered through a Celite pad, rinsing with ether. The two layers of the filtrate were separated and the aqueous layer was extracted with ether. The combined organic layers were washed with saturated NaHCO$_3$ and brine, and dried over Na$_2$SO$_4$. After filtration and careful removal of volatile solvent, the residual material was distilled under slightly reduced pressure to give the corresponding olefin as colorless oil (15 g).

A solution of the olefin (15 g, 107 mmol) in CH$_2$Cl$_2$ (210 mL) was cooled in a dry ice-acetone bath. Ozone was bubbled through the solution until the complete disappearance of starting material judged by TLC. A nitrogen stream was passed through the reaction mixture for a few minutes to drive away the excess ozone. The reaction mixture was diluted with ethanol (100 mL). NaBH$_4$ (14.2 g, 375 mmol) was added to the reaction mixture and stirring was continued while the temperature was allowed to rise to 0° C. At the completion of the reaction, water was added. After standard aqueous work-up, the corresponding alcohol was obtained as a colorless oil (15 g). The alcohol was converted to 3-(tetrahydropyran-4-yl)propyl tosylate by treatment with tosyl chloride in the presence of a base, e.g., triethylamine in CH$_2$Cl$_2$.

Example 11

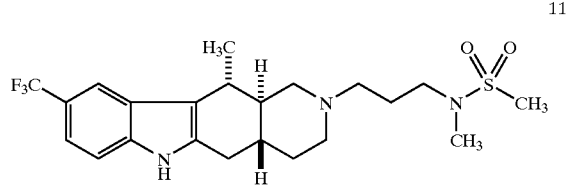

11

Compound 11 was synthesized following the procedure described in Example 5, substituting N-(3-methanesulfonyloxy-propyl)-N-methyl-methanesulfonamide for 1-(3-chloropropyl)pyrrolidin-2-one. The corresponding HCl salt was prepared by the addition of 1 N HCl in ether to a solution of the product in ethyl acetate. The HCl salt precipitated out on concentration. $^1$H NMR of 11.HCl: (CDCl$_3$)δ 11.8 (s, 1H), 7.66 (s, 1H), 7.56 (s, 1H), 7.30 (d, J=8.6 Hz, 1H), 7.18 (d, J=8.6 Hz, 1H), 3.56 (d, J=11 Hz, 1H), 3.42 (d, J=12 Hz, 1H), 3.16 (bs, 2H), 2.92 (m, 2H), 2.36 (m, 2H), 2.12–2.23 (m, 4H), 1.99 (q, J=11.7 Hz, 1H), 1.72 (d, J=12 Hz, 1H), 1.56 (bs, 2H), 1.30 (m, 1H), 0.98 (d, J=6.3 Hz, 3H). MS (ES) 458 [M+H]$^+$.

Example 12

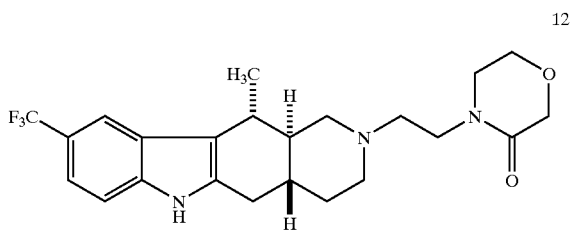

12

Compound 12 was synthesized following the procedure described in Example 5, substituting 4-(2-chloro-ethyl)-morpholin-3-one for 1-(3-chloropropyl)pyrrolidin-2-one. $^1$H NMR (DMSO-d$_6$) δ 11.2 (s, 1H), 7.77 (s, 1H), 7.44 (d, J=8.4 Hz, 1H), 7.28 (d, J=8.6 Hz, 1H), 4.02 (s, 2H), 3.81 (t, J=4.7 Hz, 2H), 3.50 (m, 1H), 3.42 (t, J=4.7 Hz, 2H), 3.30 (m, 2H), 2.92 (m, 1H), 2.75 (d, J=12 Hz, 1H), 2.60 (m, 1H), 2.40 (m, 2H), 1.91 (d, J=8.4 Hz, 1H), 1.85 (m, 1H), 1.40 (m, 2H), 1.38 (d, J=6.6 Hz, 3H), 1.25 (m, 1H). MS (ES) 436 [M+H]$^+$.

Example 13

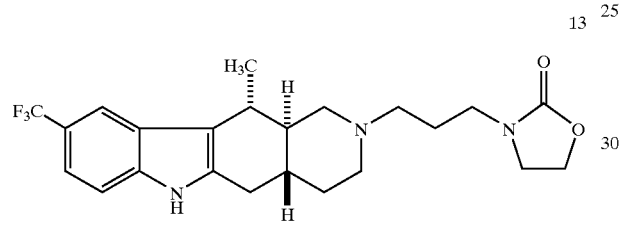

13

Compound 13 was synthesized following the procedure described in Example 5, substituting 3-(3-chloro-propyl)-oxazolidin-2-one for 1-(3-chloropropyl)pyrrolidin-2-one. $^1$H NMR (d$_6$-DMSO) δ 11.2 (s, 1H), 7.77 (s, 1H), 7.43 (d, J=8.4 Hz, 1H), 7.27 (d, J=8.6 Hz, 1H), 4.25 (t, J=8.0 Hz, 2H), 3.54 (t, J=8.0 Hz, 2H), 3.34 (m, 2H), 3.24 (t, J=12 Hz, 1H), 3.19 (t, J=7.0 Hz, 2H), 2.96 (d, J=12 Hz, 1H), 2.60 (t, J=7.0 Hz, 1H), 2.39 (m, 3H), 1.95 (m, 1H), 1.89 (d, J=7.0 Hz, 1H), 1.70 (t, J=7.0 Hz, 2H), 1.40 (m, 1H), 1.36 (d, J=6.6 Hz, 2H), 1.25 (m, 1H). MS (ES) 436 [M+H]$^+$.

Example 14

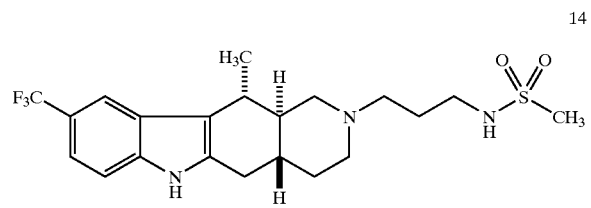

14

Compound 14 was prepared in three steps from compound 4a, as follows.

Step A

A mixture of compound 4a, (5.5 g, 17.6 mmol), N-(3-bromopropyl)phthalimide (5.5 g, 20.5 mmol), sodium bicarbonate (5.0 g, 63.1 mmol) and sodium iodide (0.50 g, 3.33 mmol) in DMF (50 mL) was heated at 90° C. overnight. The reaction mixture was diluted with ethyl acetate, washed with brine. The organic layer was dried over MgSO$_4$, filtered and concentrated. The crude product was purified by flash chromatography on silica gel, eluting with a solvent system consisting of CH$_2$Cl$_2$—MeOH—NH$_4$OH in 40:1:0.1 ratio by volume to give the desired phthalimide intermediate.

Step B

The product from step A was dissolved in ethanol (75 mL) and treated with hydrazine monohydrate (15 mL) at reflux overnight. Upon cooling to room temperature, the precipitate was removed by filtration and the filtrate was concentrated, and purified by flash chromatography on silica gel, eluting with CH$_2$Cl$_2$—MeOH—NH$_4$OH in 10:1:0.1 ratio by volume to give the corresponding amine.

Step C

Compound 14 was prepared by treating a sample of the amine compound from step B with methanesulfonyl chloride in the presence of a tertiary amine base such as triethylamine. $^1$H NMR (DMSO-d$^6$) δ 11.2 (s, 1H), 7.77 (s, 1H), 7.43 (d, J=8.4 Hz, 1H), 7.27 (d, J=8.6 Hz, 1H), 7.00 (bs, 1H), 3.31 (m, 1H), 3.30 (m, 2H), 2.90 (s, 3H), 2.78 (d, J=12 Hz, 1H), 2.60 (m, 1H), 2.40 (m, 3H), 1.95 (m, 2H), 1.68 (m, 3H), 1.45 (m, 2H), 1.37 (d, J=6.6 Hz, 3H), 1.25, (1H). MS (ES) 444 [M+H]$^+$.

Example 15

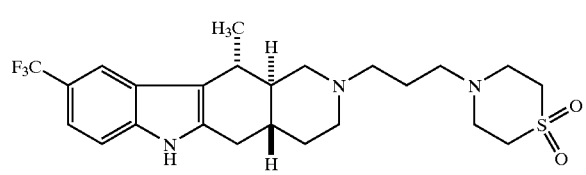

15

Compound 15 was prepared by treating a sample of the amine from step B of Example 14 with vinylsulfone in ethanol at refluxing temperature for 30 min. $^1$H NMR (d$_6$-DMSO) δ 11.2 (s, 1H), 7.77 (s, 1H), 7.43 (d, J=8.4 Hz, 1H), 7.27 (d, J=8.6 Hz, 1H), 3.33 (m, 1H), 3.08 (t, J=5.2 Hz, 4H), 2.92 (m, 1H), 2.88 (t, J=5.2 Hz, 4H), 2.78 (d, J=12 Hz, 1H), 2.60 (m, 1H), 2.40 (m, 2H), 1.89–1.96 (m, 2H), 1.62 (m, 3H), 1.42 (m, 2H), 1.38 (d, J=6.6 Hz, 3H), 1.30 (m, 1H). MS (ES) 484 [M+H]$^+$.

Example 16

The MCHR modulatory activity of the compounds of the invention can be assessed using the in vitro and in vivo assay methods described above.

Exemplary in vitro methods include fluorometric imaging plate reader (FLIPR) functional assays (see, e.g., *G Protein-Coupled Receptors* (1999) pp. 105–108 (T. Haga, G. Bernstein, eds.) CRC Press; Lembo et al. (1999) *Nature Cell Biol.* 1:267–271; Saito et al. (1999) *Nature* 400:265–269; Wood et al. (2000) *Eur. J. Pharmacol.* 396:1–8 and Miller et al. (1999) *J. Biomol. Screen.* 4:249–258) and radioligand binding assays (see, e.g., *Receptor Binding Techniques* (1999) pp. 37–47 (M. Keen, ed.) Humana Press; Buckley et al. (1989) *Mol. Pharmacol.* 35:469–476; Mihara et al. (1994) *J. Pharmacol. Exp. Ther.* 268:1122–1128; Newman et al. (2000) *Eur. J. Pharmacol.* 397:255–262 and Audinot et al. (2001) *Br. J. Pharmacol.* 133:371–378).

Exemplary compounds demonstrated MCHR1 modulatory activity.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A compound having the formula:

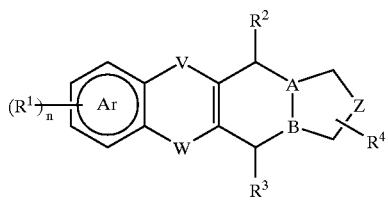

wherein

A and B independently are CR', wherein each R' is independently selected from the group consisting of hydrogen, $(C_1-C_5)$alkyl, arylalkyl, —C(O)$R^7$, —CO$_2R^8$ and —C(O)NR$^5$R$^6$;

V is either a bond and W is —N(R")—, or V is —N(R")— and W is a bond, wherein R" is hydrogen or $(C_1-C_5)$alkyl;

Z is —N(R)—CH$_2$—, wherein R is selected from the group consisting of hydrogen, $(C_1-C_7)$alkyl, heterocycloalkyl$(C_1-C_7)$alkyl, aryl, arylalkyl, —C(O)R$^7$, —CO$_2R^8$, —C(O)NR$^5$R$^6$, —S(O)$_m$NR$^5$R$^6$ and —S(O)$_mR^7$;

each $R^1$ is independently selected from the group consisting of halogen, $(C_1-C_5)$alkyl, perfluoro$(C_1-C_5)$alkyl, —OR'", —SR'", aryl, aryl$(C_1-C_5)$alkyl, —NO$_2$, —NR$^5$R$^6$, —C(O)R$^7$, —CO$_2R^8$, —C(O)NR$^5$R$^6$, —N(R$^5$)C(O)R$^7$, —N(R$^5$)CO$_2R^9$, —N(R$^7$)C(O)NR$^5$R$^6$, —S(O)$_m$NR$^5$R$^6$, —S(O)$_mR^7$, —CN and —N(R$^5$)S(O)$_mR^9$, wherein R'" is selected from the group consisting of hydrogen, $(C_1-C_5)$alkyl, aryl and aryl$(C_1-C_5)$alkyl;

$R^2$ and $R^3$ are independently selected from the group consisting of hydrogen, —OR'", =O, —CN, $(C_1-C_5)$alkyl and aryl, wherein R'" is selected from the group consisting of hydrogen, $(C_1-C_5)$alkyl, aryl and aryl$(C_1-C_5)$alkyl;

$R^4$ is selected from the group consisting of hydrogen, —OR'", —C(O)R$^7$, —CO$_2R^8$, —C(O)NR$^5$R$^6$, —CN, $(C_1-C_5)$alkyl and aryl, wherein R'" is selected from the group consisting of hydrogen, $(C_1-C_5)$alkyl, aryl and aryl$(C_1-C_5)$alkyl;

$R^5$ and $R^6$ are independently selected from the group consisting of hydrogen, alkyl, aryl and aryl$(C_1-C_5)$alkyl or combined to form a 4-, 5-, 6-, 7- or 8-membered ring containing from one to three atoms selected from the group consisting of O, N, S, and Si;

$R^7$ and $R^8$ are independently selected from the group consisting of hydrogen, alkyl, aryl and aryl$(C_1-C_5)$alkyl;

$R^9$ is selected from the group consisting of alkyl, aryl and aryl$(C_1-C_5)$alkyl;

the subscript m is an integer from 1 to 2;

the subscript n is an integer from 1 to 4; and wherein

is a substituted benzene ring;

with the proviso that $R^2$ is not hydrogen when A and B are both CH, V is a bond, and W is —N(R")—.

2. The compound of claim 1, wherein V is —N(R")—.

3. The compound of claim 1, wherein W is —N(R")—.

4. The compound of claim 1, wherein W is —NH—.

5. The compound of claim 1, wherein R is $(C_1-C_7)$alkyl or heterocycloalkyl$(C_1-C_7)$alkyl.

6. The compound of claim 1, wherein $R^2$ is $(C_1-C_5)$alkyl or aryl.

7. A compound having the formula:

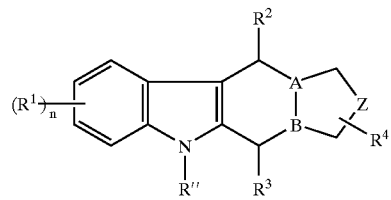

wherein

A and B independently are CR', wherein each R' is independently selected from the group consisting of hydrogen, $(C_1-C_5)$alkyl, arylalkyl, —C(O)R$^7$, —CO$_2R^8$ and —C(O)NR$^5$R$^6$;

Z is —N(R)—CH$_2$—, wherein R is heterocycloalkyl$(C_1-C_7)$alkyl;

R" is hydrogen or $(C_1-C_5)$alkyl;

each $R^1$ is independently selected from the group consisting of hydrogen, halogen, $(C_1-C_5)$alkyl, perfluoro$(C_1-C_5)$alkyl, —OR'", —SR'", aryl, aryl$(C_1-C_5)$alkyl, —NO$_2$, —NR$^5$R$^6$, —C(O)R$^7$, —CO$_2R^8$, —C(O)NR$^5$R$^6$, —N(R$^5$)C(O)R$^7$, —N(R$^5$)CO$_2R^9$, —N(R$^7$)C(O)NR$^5$R$^6$, —S(O)$_m$NR$^5$R$^6$, —S(O)$_mR^7$, —CN and —N(R$^5$)S(O)$_mR^9$, wherein R'" is selected from the group consisting of hydrogen, $(C_1-C_5)$alkyl, aryl and aryl$(C_1-C_5)$alkyl;

$R^2$ and $R^3$ are independently selected from the group consisting of hydrogen, —OR'", =O, —CN, $(C_1-C_5)$alkyl and aryl, wherein R'" is selected from the group consisting of hydrogen, $(C_1-C_5)$alkyl, aryl and aryl$(C_1-C_5)$alkyl;

$R^4$ is selected from the group consisting of hydrogen, —OR'", —C(O)R$^7$, —CO$_2R^8$, —C(O)NR$^5$R$^6$, —CN, $(C_1-C_5)$alkyl and aryl, wherein R'" is selected from the group consisting of hydrogen, $(C_1-C_5)$alkyl, aryl and aryl$(C_1-C_5)$alkyl;

$R^5$ and $R^6$ are independently selected from the group consisting of hydrogen, alkyl, aryl and aryl$(C_1-C_5)$alkyl or combined to form a 4-, 5-, 6-, 7- or 8-membered ring containing from one to three atoms selected from the group consisting of O, N, S, and Si;

$R^7$ and $R^8$ are independently selected from the group consisting of hydrogen, alkyl, aryl and aryl$(C_1-C_5)$alkyl;

$R^9$ is selected from the group consisting of alkyl, aryl and aryl$(C_1-C_5)$alkyl;

the subscript m is an integer from 1 to 2; and the subscript n is an integer from 0 to 4;
with the proviso that $R^2$ is not hydrogen when A and B are both CH.

8. The compound of claim 7, wherein $R^2$ is $(C_1–C_5)$alkyl or aryl.

9. The compound of claim 1, having the formula:

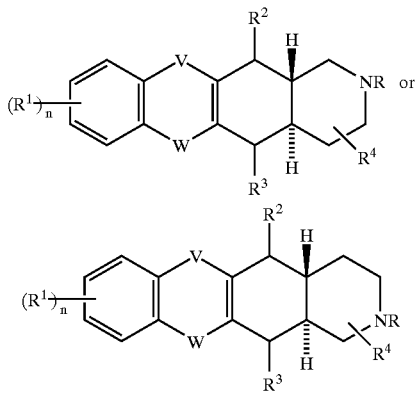

wherein
V is either a bond and W is —N(R")—, or V is —N(R")— and W is a bond, wherein R" is hydrogen or $(C_1–C_5)$alkyl;
R is selected from the group consisting of hydrogen, $(C_1–C_7)$alkyl, heterocycloalkyl$(C_1–C_7)$alkyl, aryl, arylalkyl, —C(O)$R^7$, $CO_2R^8$, —C(O)$NR^5R^6$, —S(O)$_m$$NR^5R^6$ and —S(O)$_m$$R^7$;
each $R^1$ is independently selected from the group consisting of halogen, $(C_1–C_5)$alkyl, perfluoro$(C_1–C_5)$alkyl, —OR'", —SR'", aryl, aryl$(C_1–C_5)$alkyl, —$NO_2$, —$NR^5R^6$, —C(O)$R^7$, —$CO_2R^8$, —C(O)$NR^5R^6$, —N($R^5$)C(O)$R^7$, —N($R^5$)$CO_2R^9$, —N($R^7$)C(O)$NR^5R^6$, —S(O)$_m$$NR^5R^6$, —S(O)$_m$$R^7$, —CN and —N($R^5$)S(O)$_m$$R^9$, wherein R'" is selected from the group consisting of hydrogen, $(C_1–C_5)$alkyl, aryl and aryl$(C_1–C_5)$alkyl;
$R^2$ and $R^3$ are independently selected from the group consisting of hydrogen, —OR'", =O, —CN, $(C_1–C_5)$alkyl and aryl, wherein R'" is selected from the group consisting of hydrogen, $(C_1–C_5)$alkyl, aryl and aryl $(C_1–C_5)$alkyl;
$R^4$ is selected from the group consisting of hydrogen, —OR'", —C(O)$R^7$, —$CO_2R^8$, —C(O)$NR^5R^6$, —CN, $(C_1–C_5)$alkyl and aryl, wherein R'" is selected from the group consisting of hydrogen, $(C_1–C_5)$alkyl, aryl and aryl$(C_1–C_5)$alkyl;
$R^5$ and $R^6$ are independently selected from the group consisting of hydrogen, alkyl, aryl and aryl$(C_1–C_5)$alkyl or combined to form a 4-, 5-, 6-, 7- or 8-membered ring containing from one to three atoms selected from the group consisting of O, N, S, and Si;
$R^7$ and $R^8$ are independently selected from the group consisting of hydrogen, alkyl, aryl and aryl$(C_1–C_5)$alkyl;
$R^9$ is selected from the group consisting of alkyl, aryl and aryl$(C_1–C_5)$alkyl;
the subscript m is an integer from 1 to 2; and
the subscript n is an integer from 1 to 4;
with the proviso that $R^2$ is not hydrogen when V is a bond and W is —N(R")—.

10. The compound of claim 9, wherein V is a bond and W is —N(R")—.

11. The compound of claim 10 or a pharmaceutically acceptable salt or solvate thereof, wherein said compound is selected from the group consisting of:

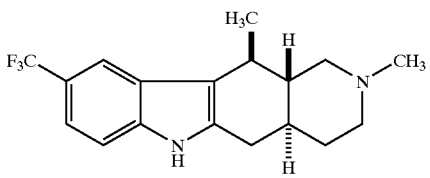

,

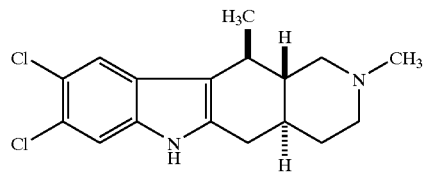

,

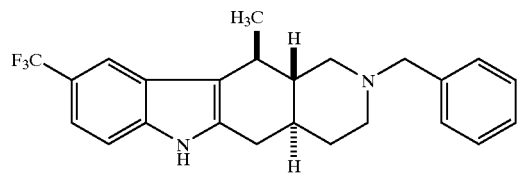

,

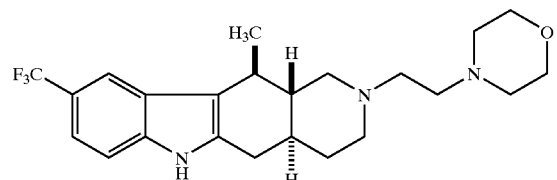

,

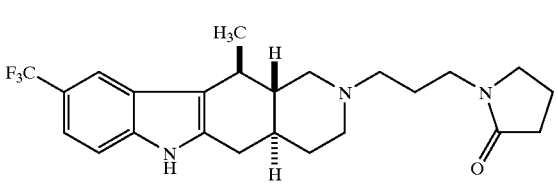

,

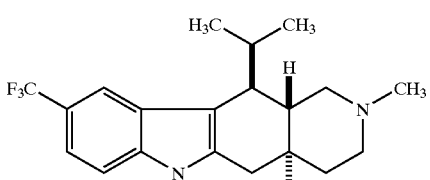

,

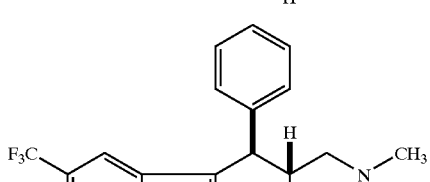

,

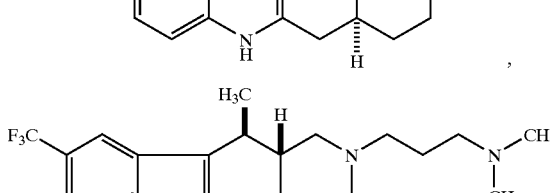

,

-continued

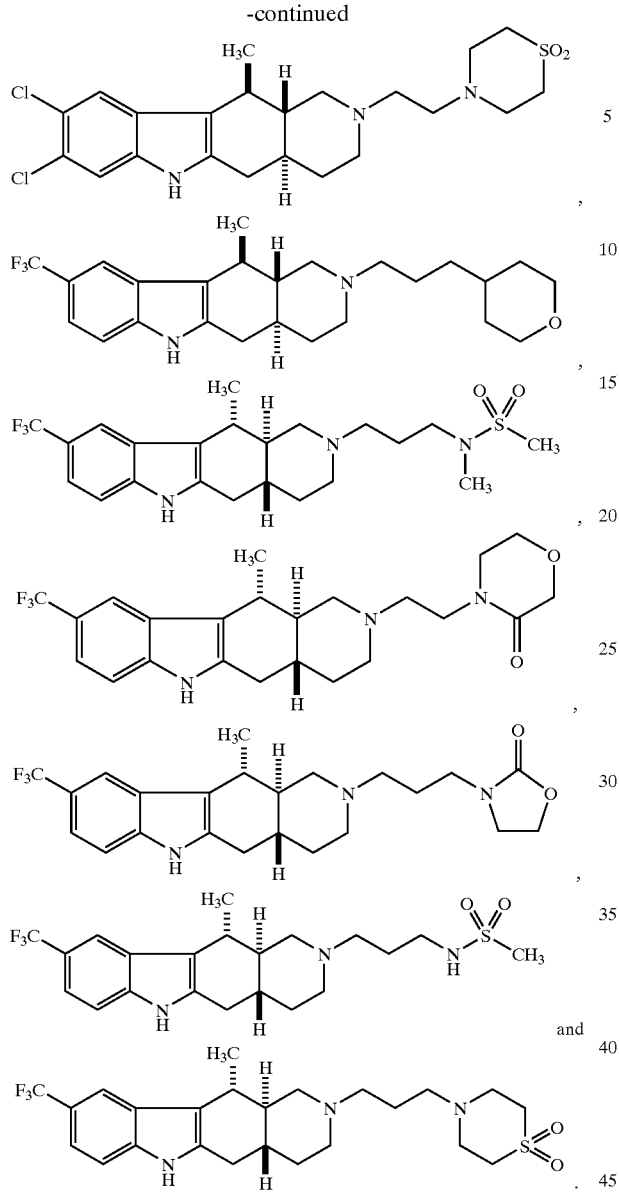

12. A pharmaceutical composition comprising a pharmaceutically acceptable carrier or excipient and a compound having the formula:

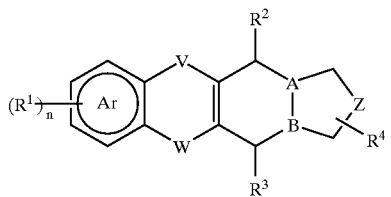

wherein
A and B independently are CR', wherein R' is independently selected from the group consisting of hydrogen, (C$_1$–C$_5$)alkyl, arylalkyl, —C(O)R$^7$, —CO$_2$R$^8$ and —C(O)NR$^5$R$^6$;
V is either a bond and W is —N(R")—, or V is —N(R")— and W is a bond, wherein R" is hydrogen or (C$_1$–C$_5$)alkyl;

Z is —N(R)—CH$_2$—, wherein R is selected from the group consisting of hydrogen, (C$_1$–C$_7$)alkyl, heterocycloalkyl(C$_1$–C$_7$)alkyl, aryl, arylalkyl, —C(O)R$^7$, —CO$_2$R$^8$, —C(O)NR$^5$R$^6$, —S(O)$_m$NR$^5$R$^6$ and —S(O)$_m$R$^7$;

each R$^1$ is independently selected from the group consisting of hydrogen, halogen, (C$_1$–C$_5$)alkyl, perfluoro(C$_1$–C$_5$)alkyl, —OR'", —SR'", aryl, arylalkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, —S(O)$_m$R$^7$, —CN and —N(R$^5$)S(O)$_m$R$^9$, wherein R'" is selected from the group consisting of hydrogen, (C$_1$–C$_5$) alkyl, aryl and aryl(C$_1$–C$_5$)alkyl;

R$^2$ and R$^3$ are independently selected from the group consisting of hydrogen, —OR'", =O, —CN, (C$_1$–C$_5$)alkyl and aryl, wherein R'" is selected from the group consisting of hydrogen, (C$_1$–C$_5$)alkyl, aryl and aryl(C$_1$–C$_5$)alkyl;

R$^4$ is selected from the group consisting of hydrogen, —OR'", —C(O)R$^7$, —CO$_2$R$^8$, —C(O)NR$^5$R$^6$, —CN, (C$_1$–C$_5$)alkyl and aryl, wherein R'" is selected from the group consisting of hydrogen, (C$_1$–C$_5$) alkyl, aryl and aryl(C$_1$–C$_5$)alkyl;

R$^5$ and R$^6$ are independently selected from the group consisting of hydrogen, alkyl, aryl and arylalkyl or combined to form a 4-, 5-, 6-, 7- or 8-membered ring containing from one to three atoms selected from the group consisting of O, N, S, and Si;

R$^7$ and R$^8$ are independently selected from the group consisting of hydrogen, alkyl, aryl and arylalkyl;

R$^9$ is selected from the group consisting of alkyl, aryl and arylalkyl;

the subscript m is an integer from 1 to 2;
the subscript n is an integer from 0 to 4; and

is a benzene ring;
with the proviso that R$^2$ is not hydrogen when A and B are both CH, V is a bond, and W is —N(R")—.

13. A method for treating a condition or disorder selected from the group consisting of obesity, an eating disorder, an anxiety disorder and a mood disorder, comprising
administering to a subject in need thereof a therapeutically effective amount of a compound having the formula:

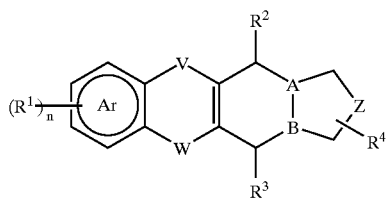

wherein
A and B independently are CR', wherein R' is independently selected from the group consisting of hydrogen, (C$_1$–C$_5$)alkyl, arylalkyl, —C(O)R$^7$, —CO$_2$R$^8$ and —C(O)NR$^5$R$^6$;
V is either a bond and W is —N(R")—, or V is —N(R")— and W is a bond, wherein R" is hydrogen or (C$_1$–C$_5$)alkyl;

Z is —N(R)—CH$_2$—, wherein R is selected from the group consisting of hydrogen, (C$_1$–C$_7$)alkyl, heterocycloalkyl(C$_1$–C$_7$)alkyl, aryl, arylalkyl, —C(O)R$^7$, —CO$_2$R$^8$, —C(O)NR$^5$R$^6$, —S(O)$_m$NR$^5$R$^6$ and —S(O)$_m$R$^7$;

each R$^1$ is independently selected from the group consisting of hydrogen, halogen, (C$_1$–C$_5$)alkyl, perfluoro(C$_1$–C$_5$)alkyl, —OR''', —SR''', aryl, arylalkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^7$)C(O)NR$^5$R$^6$, —S(O)$_m$NR$^5$R$^6$, —S(O)$_m$R$^7$, —CN and —N(R$^5$)S(O)$_m$R$^9$, wherein R''' is selected from the group consisting of hydrogen, (C$_1$–C$_5$)alkyl, aryl and aryl(C$_1$–C$_5$)alkyl;

R$^2$ and R$^3$ are independently selected from the group consisting of hydrogen, —OR''', =O, —CN, (C$_1$–C$_5$)alkyl and aryl, wherein R''' is selected from the group consisting of hydrogen, (C$_1$–C$_5$)alkyl, aryl and aryl(C$_1$–C$_5$)alkyl;

R$^4$ is selected from the group consisting of hydrogen, —OR''', —C(O)R$^7$, —CO$_2$R$^8$, —C(O)NR$^5$R$^6$, —CN, (C$_1$–C$_5$)alkyl and aryl, wherein R''' is selected from the group consisting of hydrogen, (C$_1$–C$_5$) alkyl, aryl and aryl(C$_1$–C$_5$)alkyl;

R$^5$ and R$^6$ are independently selected from the group consisting of hydrogen, alkyl, aryl and arylalkyl or combined to form a 4-, 5-, 6-, 7- or 8-membered ring containing from one to three atoms selected from the group consisting of O, N, S, and Si;

R$^7$ and R$^8$ are independently selected from the group consisting of hydrogen, alkyl, aryl and arylalkyl;

R$^9$ is selected from the group consisting of alkyl, aryl and arylalkyl;

the subscript m is an integer from 1 to 2;

the subscript n is an integer from 0 to 4; and

is a benzene ring;

with the proviso that R$^2$ is not hydrogen when A and B are both CH, V is a bond, and W is —N(R'')—.

14. The method of claim 13 wherein said compound modulates melanin-concentrating hormone receptor ("MCHR").

15. The method of claim 13 wherein said compound is administered orally.

16. The method of claim 13 wherein said compound is administered parenterally.

17. A method for modifying eating behavior, comprising administering to a subject in need thereof a therapeutically effective amount of a compound having the formula:

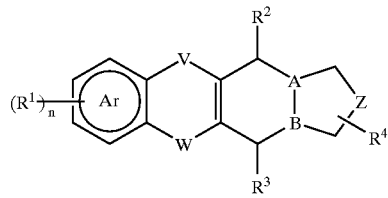

wherein
A and B independently are CR', wherein R' is independently selected from the group consisting of hydrogen, (C$_1$–C$_5$)alkyl, arylalkyl, —C(O)R$^7$, —CO$_2$R$^8$ and —C(O)NR$^5$R$^6$;

V is either a bond and W is —N(R'')—, or V is —N(R'')— and W is a bond, wherein R'' is hydrogen or (C$_1$–C$_5$)alkyl;

Z is —N(R)—CH$_2$—, wherein R is selected from the group consisting of hydrogen, (C$_1$–C$_7$)alkyl, heterocycloalkyl(C$_1$–C$_7$)alkyl, aryl, arylalkyl, —C(O)R$^7$, —CO$_2$R$^8$, —C(O)NR$^5$R$^6$, —S(O)$_m$NR$^5$R$^6$ and —S(O)$_m$R$^7$;

each R$^1$ is independently selected from the group consisting of hydrogen, halogen, (C$_1$–C$_5$)alkyl, perfluoro(C$_1$–C$_5$)alkyl, —OR''', —SR''', aryl, arylalkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, —S(O)$_m$R$^7$, —CN and —N(R$^5$)S(O)$_m$R$^9$, wherein R''' is selected from the group consisting of hydrogen, (C$_1$–C$_5$) alkyl, aryl and aryl(C$_1$–C$_5$)alkyl;

R$^2$ and R$^3$ are independently selected from the group consisting of hydrogen, —OR''', =O, —CN, (C$_1$–C$_5$)alkyl and aryl, wherein R''' is selected from the group consisting of hydrogen, (C$_1$–C$_5$)alkyl, aryl and aryl(C$_1$–C$_5$)alkyl;

R$^4$ is selected from the group consisting of hydrogen, —OR''', —C(O)R$^7$, —CO$_2$R$^8$, —C(O)NR$^5$R$^6$, —CN, (C$_1$–C$_5$)alkyl and aryl, wherein R''' is selected from the group consisting of hydrogen, (C$_1$–C$_5$) alkyl, aryl and aryl(C$_1$–C$_5$)alkyl;

R$^5$ and R$^6$ are independently selected from the group consisting of hydrogen, alkyl, aryl and arylalkyl or combined to form a 4-, 5-, 6-, 7- or 8-membered ring containing from one to three atoms selected from the group consisting of O, N, S, and Si;

R$^7$ and R$^8$ are independently selected from the group consisting of hydrogen, alkyl, aryl and arylalkyl;

R$^9$ is selected from the group consisting of alkyl, aryl and arylalkyl;

the subscript m is an integer from 1 to 2;

the subscript n is an integer from 0 to 4; and

is a benzene ring;

with the proviso that R$^2$ is not hydrogen when A and B are both CH, V is a bond, and W is —N(R'')—.

18. The method of claim 17, wherein food intake is decreased.

19. The method of claim 17, wherein food intake is increased.

20. The method of claim 13, wherein said eating disorder is anorexia nervosa.

21. The method of claim 13, wherein said anxiety disorder is selected from the group consisting of anxiety, panic disorder and obsessive-compulsive disorder.

22. The method of claim 13, wherein said mood disorder is depression.

23. A method for modulating melanin-concentrating hormone receptor ("MCHR"), comprising contacting a cell with a compound having the formula:

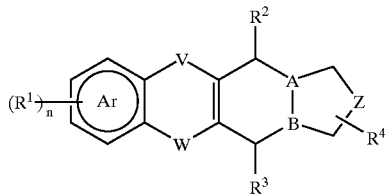

wherein
- A and B independently are CR', wherein R' is independently selected from the group consisting of hydrogen, $(C_1-C_5)$alkyl, arylalkyl, —C(O)R$^7$, —CO$_2$R$^8$ and —C(O)NR$^5$R$^6$;
- V is either a bond and W is —N(R")—, or V is —N(R")— and W is a bond, wherein R" is hydrogen or $(C_1-C_5)$alkyl;
- Z is —N(R)—CH$_2$—, wherein R is selected from the group consisting of hydrogen, $(C_1-C_7)$alkyl, heterocycloalkyl$(C_1-C_7)$alkyl, aryl, arylalkyl, —C(O)R$^7$, —CO$_2$R$^8$, —C(O)NR$^5$R$^6$, —S(O)$_m$NR$^5$R$^6$ and —S(O)$_m$R$^7$;
- each R$^1$ is independently selected from the group consisting of hydrogen, halogen, $(C_1-C_5)$alkyl, perfluoro$(C_1-C_5)$alkyl, —OR'", —SR'", aryl, arylalkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, —S(O)$_m$R$^7$, —CN and N(R$^5$)S(O)$_m$R$^9$, wherein R'" is selected from the group consisting of hydrogen, $(C_1-C_5)$ alkyl, aryl and aryl$(C_1-C_5)$alkyl;
- R$^2$ and R$^3$ are independently selected from the group consisting of hydrogen, —OR'", =O, —CN, $(C_1-C_5)$alkyl and aryl, wherein R'" is selected from the group consisting of hydrogen, $(C_1-C_5)$alkyl, aryl and aryl$(C_1-C_5)$alkyl;
- R$^4$ is selected from the group consisting of hydrogen, —OR'", —C(O)R$^7$, —CO$_2$R$^8$, —C(O)NR$^5$R$^6$, —CN, $(C_1-C_5)$alkyl and aryl, wherein R'" is selected from the group consisting of hydrogen, $(C_1-C_5)$ alkyl, aryl and aryl$(C_1-C_5)$alkyl;
- R$^5$ and R$^6$ are independently selected from the group consisting of hydrogen, alkyl, aryl and arylalkyl or combined to form a 4-, 5-, 6-, 7- or 8-membered ring containing from one to three atoms selected from the group consisting of O, N, S, and Si;
- R$^7$ and R$^8$ are independently selected from the group consisting of hydrogen, alkyl, aryl and arylalkyl;
- R$^9$ is selected from the group consisting of alkyl, aryl and arylalkyl;
- the subscript m is an integer from 1 to 2;
- the subscript n is an integer from 0 to 4; and

is a benzene ring;
with the proviso that R$^2$ is not hydrogen when A and B are both CH, V is a bond, and W is —N(R")—.

24. The method of claim 23, wherein said compound is an MCHR antagonist.

25. The method of claim 23, wherein said compound is an MCHR agonist.

26. The compound of claim 10, having the formula:

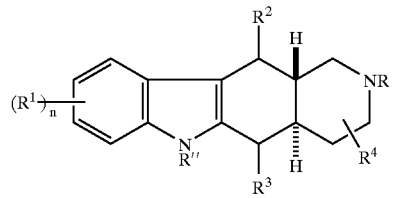

wherein
- R is selected from the group consisting of hydrogen, $(C_1-C_7)$alkyl, heterocycloalkyl$(C_1-C_7)$alkyl, aryl, arylalkyl, —C(O)R$^7$, —CO$_2$R$^8$, —C(O)NR$^5$R$^6$, —S(O)$_m$NR$^5$R$^6$ and —S(O)$_m$R$^7$;
- each R$^1$ is independently selected from the group consisting of halogen, $(C_1-C_5)$alkyl, perfluoro $(C_1-C_5)$alkyl, —OR'", —SR'", aryl, aryl$(C_1-C_5)$ alkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, S(O)$_m$R$^7$, —CN and —N(R$^5$)S(O)$_m$R$^9$, wherein R'" is selected from the group consisting of hydrogen, $(C_1-C_5)$ alkyl, aryl and aryl$(C_1-C_5)$alkyl;
- R$^2$ and R$^3$ are independently selected from the group consisting of hydrogen, —OR'", =O, —CN, $(C_1-C_5)$alkyl and aryl, wherein R'" is selected from the group consisting of hydrogen, $(C_1-C_5)$alkyl, aryl and aryl$(C_1-C_5)$alkyl;
- R$^4$ is selected from the group consisting of hydrogen —OR'", —C(O)R$^7$, —CO$_2$R$^8$, —C(O)NR$^5$R$^6$, —CN, $(C_1-C_5)$alkyl and aryl, wherein R'" is selected from the group consisting of hydrogen, $(C_1-C_5)$ alkyl, aryl and aryl$(C_1-C_5)$alkyl;
- R$^5$ and R$^6$ are independently selected from the group consisting of hydrogen, alkyl, aryl and aryl$(C_1-C_5)$ alkyl or combined to form a 4-, 5-, 6-, 7- or 8-membered ring containing from one to three atoms selected from the group consisting of O, N, S, and Si;
- R$^7$ and R$^8$ are independently selected from the group consisting of hydrogen, alkyl, aryl and aryl$(C_1-C_5)$ alkyl;
- R$^9$ is selected from the group consisting of alkyl, aryl and aryl$(C_1-C_5)$alkyl;
- the subscript m is an integer from 1 to 2; and
- the subscript n is an integer from 1 to 4;
- with the proviso that R$^2$ is not hydrogen.

27. A compound as in claim 1, in which the compound is a pharmaceutically acceptable salt.

28. A compound as in claim 1, in which the compound is a solvate or hydrate.

29. A compound as in claim 1, in which the compound is in a prodrug form.

30. A compound as in claim 7, in which the compound is a pharmaceutically acceptable salt.

31. A compound as in claim 7, in which the compound is a solvate or hydrate.

32. A compound as in claim 7, in which the compound is in a prodrug form.

33. The pharmaceutical composition of Claim 12, wherein the compound is a pharmaceutically acceptable salt.

34. The pharmaceutical composition of claim 12, wherein the compound is a solvate or hydrate.

35. The pharmaceutical composition of claim 12, where the compound is in a prodrug form.

36. The composition of claim 12, wherein

of said compound is a substituted benzene ring, said subscript n is an integer from 1 to 4, and each $R^1$ is independently selected from the group consisting of halogen, $(C_1-C_5)$alkyl, perfluoro$(C_1-C_5)$alkyl, —OR''', —SR''', aryl, aryl$(C_1-C_5)$alkyl, —NO$_2$, —NR$^5$R$^6$, —C(O)R$^7$, —C(O)$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, —S(O)$_m$R$^7$, —CN and —N(R$^5$)S(O)$_m$R$^9$, where in R''' is selected from the group consisting of hydrogen, $(C_1-C_5)$alkyl, aryl and aryl$(C_1-C_5)$alkyl.

37. The composition of claim 12, wherein R of said compound is $(C_1-C_7)$alkyl or heterocycloalkyl$(C_1-C_7)$alkyl.

38. The composition of claim 12, wherein said compound is selected from the group consisting of:

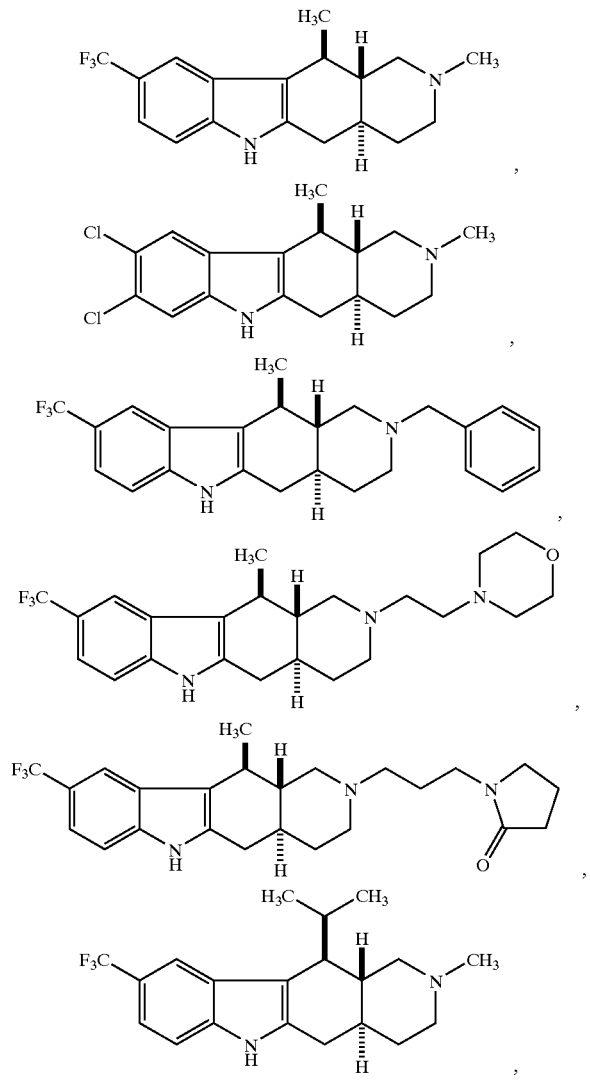

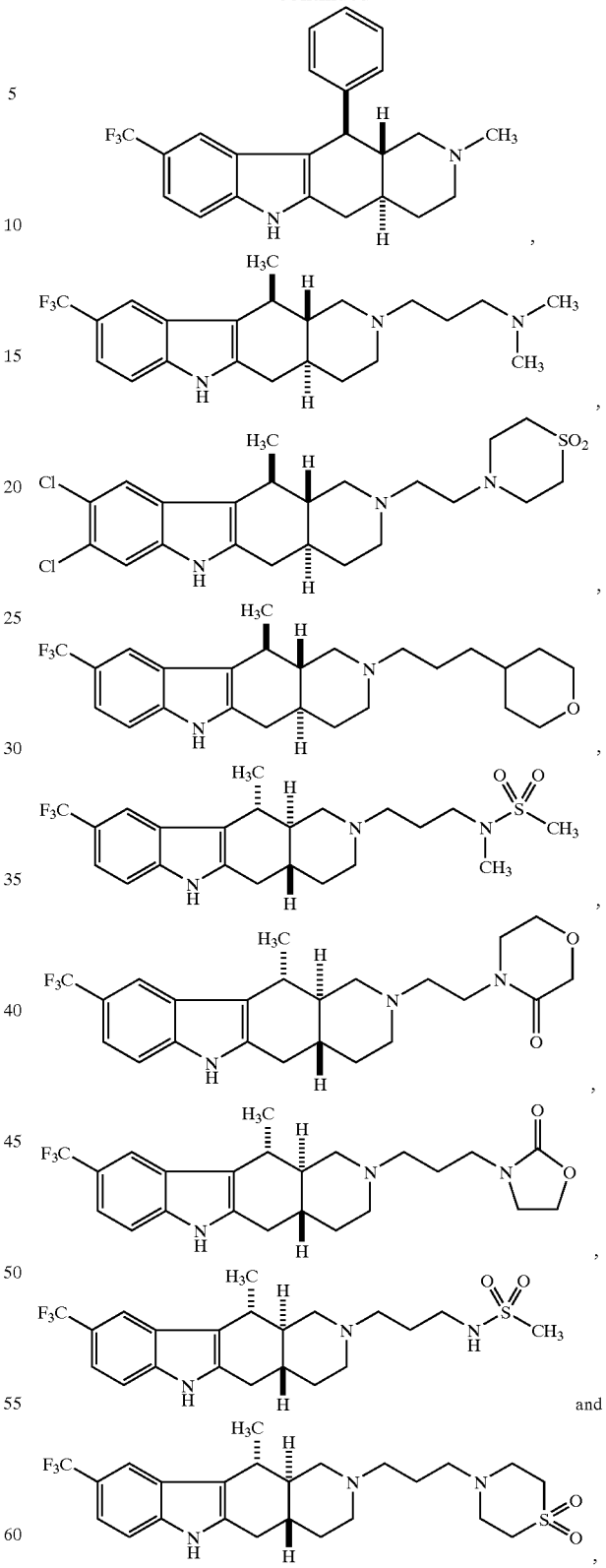

and salts thereof.

39. The method of claim 13, wherein said condition or disorder is obesity.

40. The method of claim 13, wherein said condition or disorder is an eating disorder.

41. The method of claim 13, wherein said condition or disorder is an anxiety disorder.

42. The method of claim 13, wherein said condition or disorder is a mood disorder.

43. The method of claim 13, wherein said subject is a human.

44. The method of claim 13, wherein

of said compound is a substituted benzene ring, said subscript n is an integer from 1 to 4, and each $R^1$ is independently selected from the group consisting of halogen, $(C_1-C_5)$alkyl, perfluoro$(C_1-C_5)$alkyl, —OR''', —SR''', aryl, aryl$(C_1-C_5)$alkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, —S(O)$_m$R$^7$, —CN and —N(R$^5$)S(O)$_m$R$^9$, wherein R''' is selected from the group consisting of hydrogen, $(C_1-C_5)$alkyl, aryl and aryl$(C_1-C_5)$alkyl.

45. The method of claim 17, wherein

of said compound is a substituted benzene ring, said subscript n is an integer from 1 to 4, and each $R^1$ is independently selected from the group consisting of halogen, $(C_1-C_5)$alkyl, perfluoro$(C_1-C_5)$alkyl, —OR''', —SR''', aryl, aryl$(C_1-C_5)$alkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, —S(O)$_m$R$^7$, —CN and —N(R$^5$)S(O)$_m$R$^9$, wherein R''' is selected from the group consisting of hydrogen, $(C_1-C_5)$alkyl, aryl and aryl$(C_1-C_5)$alkyl.

46. The method of claim 23, wherein

of said compound is a substituted benzene ring, said subscript n is an integer from 1 to 4, and each $R^1$ is independently selected from the group consisting of halogen, $(C_1-C_5)$alkyl, perfluoro$(C_1-C_5)$alkyl, —OR''', —SR''', aryl, aryl$(C_1-C_5)$alkyl, —NO$_2$, —NR$^5$R$^6$, —C(O)R$^7$, —CO$_2$R$^8$, —C(O)NR$^5$R$^6$, —N(R$^5$)C(O)R$^7$, —N(R$^5$)CO$_2$R$^9$, —N(R$^7$)C(O)NR$^5$R$^6$, —S(O)$_m$NR$^5$R$^6$, —S(O)$_m$R$^7$, —CN and —N(R$^5$)S(O)$_m$R$^9$, wherein R''' is selected from the group consisting of hydrogen, $(C_1-C_5)$alkyl, aryl and aryl$(C_1-C_5)$alkyl.

47. The method of claim 13, wherein said compound is selected from the group consisting of:

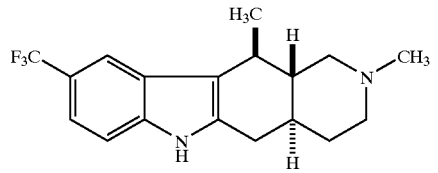

,

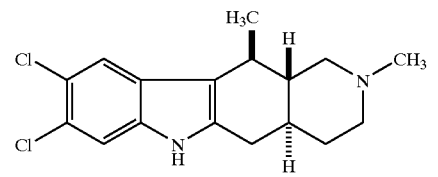

,

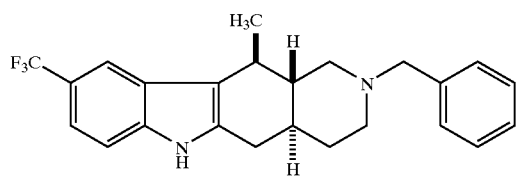

,

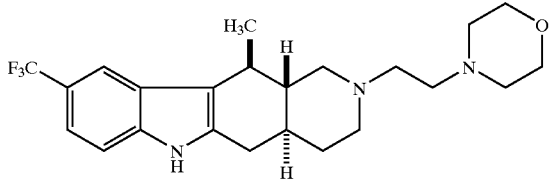

,

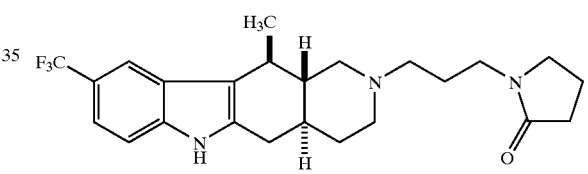

,

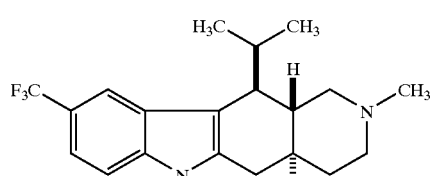

,

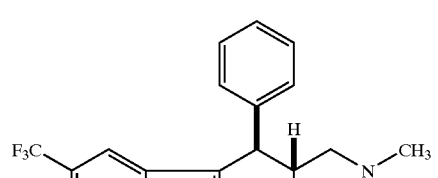

,

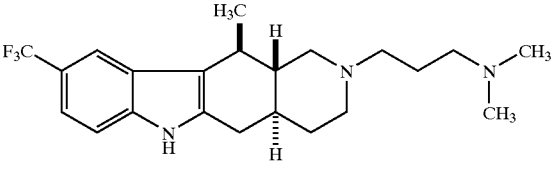

,

-continued
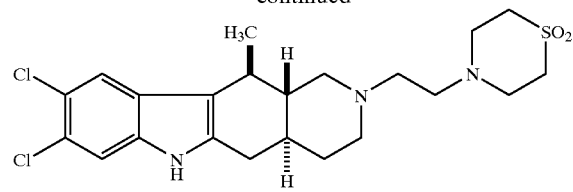
,
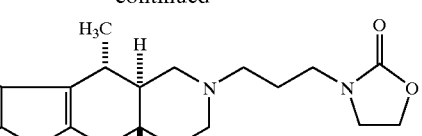
,
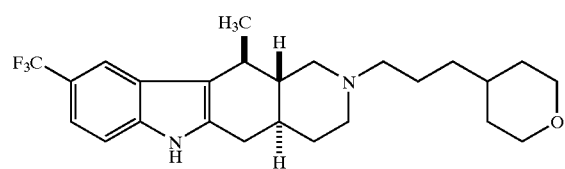
,
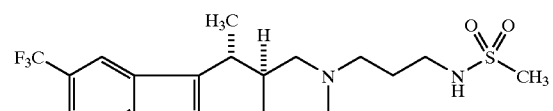
and
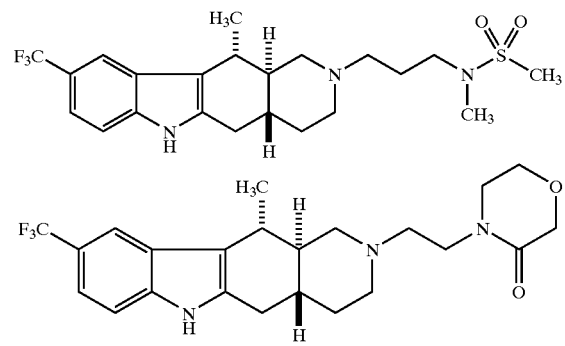
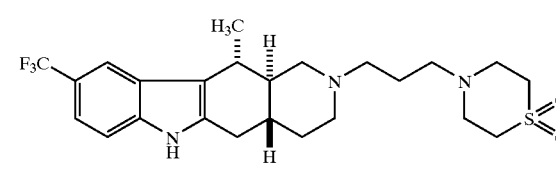
,
and salts thereof.
* * * * *